(12) United States Patent
Hirota et al.

(10) Patent No.: US 8,585,775 B2
(45) Date of Patent: Nov. 19, 2013

(54) ASSIST DEVICE

(75) Inventors: Takashi Hirota, Kyoto (JP); Mayumi Yamaguchi, Kanagawa (JP); Konami Izumi, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 79 days.

(21) Appl. No.: 12/068,451

(22) Filed: Feb. 6, 2008

(65) Prior Publication Data
US 2008/0211302 A1 Sep. 4, 2008

(30) Foreign Application Priority Data
Feb. 9, 2007 (JP) ................................. 2007-029916

(51) Int. Cl.
*A61F 2/72* (2006.01)
*A61F 2/54* (2006.01)

(52) U.S. Cl.
USPC .................................. 623/25; 623/24; 623/57

(58) Field of Classification Search
USPC .................................. 623/24, 25, 57; 700/258
See application file for complete search history.

(56) References Cited

U.S. PATENT DOCUMENTS

| | | | | |
|---|---|---|---|---|
| 51,238 | A | * 11/1865 | Snellerberg | 623/61 |
| 3,405,715 | A | * 10/1968 | Hagfors | 607/118 |
| 4,685,925 | A | * 8/1987 | Childress et al. | 623/25 |
| 5,843,142 | A | 12/1998 | Sultan | |
| 5,903,291 | A | * 5/1999 | Yoshimura et al. | 347/48 |
| 6,164,284 | A | 12/2000 | Schulman et al. | |
| 6,185,452 | B1 | 2/2001 | Schulman et al. | |
| 6,208,894 | B1 | 3/2001 | Schulman et al. | |
| 6,315,721 | B2 | 11/2001 | Schulman et al. | |
| 6,564,807 | B1 | 5/2003 | Schulman et al. | |

(Continued)

FOREIGN PATENT DOCUMENTS

| | | |
|---|---|---|
| EP | 1343112 A | 9/2003 |
| EP | 1 508 296 | 2/2005 |

(Continued)

OTHER PUBLICATIONS

FET Transistor, http://32.museumpessoa.com/fettraansistor.html, 5 pages, accessed Dec. 6, 2010.*

(Continued)

*Primary Examiner* — David Isabella
*Assistant Examiner* — Marcia Hoffman
(74) *Attorney, Agent, or Firm* — Eric J. Robinson; Robinson Intellectual Property Law Office, P.C.

(57) ABSTRACT

The present invention provides a higher-performance assist device which is safer by using a wireless charging technique. The assist device includes a detecting portion and an assist device driving portion. The detecting portion includes a sensor, a first transmitting/receiving circuit, a first data processing circuit, a first charging circuit, and a first battery. The assist device driving portion includes a driving portion, a second data processing circuit, a second transmitting/receiving circuit, a second charging circuit, and a second battery. Electromagnetic waves are transmitted from the second transmitting/receiving circuit provided in the assist device driving portion, and the first transmitting/receiving circuit provided in the detecting portion receives the electromagnetic waves. Induced electromotive force generated at this time is input to the first charging circuit through the first data processing circuit provided in the detecting portion, and the first battery provided in the detecting portion is charged.

21 Claims, 13 Drawing Sheets

(56) References Cited

U.S. PATENT DOCUMENTS

| | | |
|---|---|---|
| 6,695,885 B2 | 2/2004 | Schulman et al. |
| 7,107,103 B2 | 9/2006 | Schulman et al. |
| 7,114,502 B2 | 10/2006 | Schulman et al. |
| 7,137,998 B2 | 11/2006 | Bédard |
| 7,147,667 B2 | 12/2006 | Bédard |
| 7,255,577 B2 * | 8/2007 | Graham et al. ............. 439/76.1 |
| 7,302,296 B1 | 11/2007 | Hoffer |
| 7,314,443 B2 | 1/2008 | Jordan et al. |
| 7,314,490 B2 | 1/2008 | Bédard et al. |
| 7,460,911 B2 | 12/2008 | Cosendai et al. |
| 7,513,257 B2 | 4/2009 | Schulman et al. |
| 7,551,967 B1 * | 6/2009 | Karicherla et al. ........... 607/122 |
| 7,808,206 B2 | 10/2010 | Nagatsuka et al. |
| 7,898,215 B2 | 3/2011 | Nagatsuka et al. |
| 7,959,552 B2 | 6/2011 | Jordan et al. |
| 8,054,037 B2 | 11/2011 | Nagatsuka et al. |
| 2002/0198604 A1 | 12/2002 | Schulman et al. |
| 2004/0006264 A1 * | 1/2004 | Mojarradi et al. ............ 600/378 |
| 2004/0011366 A1 | 1/2004 | Schulman et al. |
| 2004/0049290 A1 | 3/2004 | Bedard |
| 2004/0181289 A1 | 9/2004 | Bedard et al. |
| 2005/0075682 A1 | 4/2005 | Schulman et al. |
| 2005/0104577 A1 | 5/2005 | Matei et al. |
| 2006/0122710 A1 | 6/2006 | Bedard |
| 2006/0122711 A1 | 6/2006 | Bedard et al. |
| 2006/0155386 A1 | 7/2006 | Wells et al. |
| 2006/0293578 A1 * | 12/2006 | Rennaker, II ................. 600/378 |
| 2008/0092911 A1 | 4/2008 | Schulman et al. |
| 2008/0210762 A1 * | 9/2008 | Osada et al. .................. 235/492 |

FOREIGN PATENT DOCUMENTS

| | | |
|---|---|---|
| EP | 1 508 302 | 2/2005 |
| EP | 1 647 300 | 4/2006 |
| EP | 1 666 087 | 6/2006 |
| EP | 1 702 648 | 9/2006 |
| EP | 1 709 992 | 10/2006 |
| EP | 2 064 992 | 6/2009 |
| JP | 11-113866 | 4/1999 |
| JP | 2001-167197 A | 6/2001 |
| JP | 2005-034508 A | 2/2005 |
| JP | 2005-518914 | 6/2005 |
| JP | 2005-334675 | 12/2005 |
| JP | 2006-239447 | 9/2006 |
| JP | 2007-011098 A | 1/2007 |
| WO | WO 98/37926 | 9/1998 |
| WO | WO 98/42405 | 10/1998 |
| WO | WO 98/43700 | 10/1998 |
| WO | WO 98/43701 | 10/1998 |
| WO | WO 01/02054 | 1/2001 |
| WO | WO 01/13778 | 3/2001 |
| WO | WO 03/000161 | 1/2003 |
| WO | WO 03/039652 | 5/2003 |
| WO | WO-03/077191 | 9/2003 |
| WO | WO 2004/017871 | 3/2004 |
| WO | WO 2004/017872 | 3/2004 |
| WO | WO 2004/017873 | 3/2004 |
| WO | WO 2004/073491 | 9/2004 |
| WO | WO 2005/051248 | 6/2005 |

OTHER PUBLICATIONS

Search Report (Application No. 08002060.5) Dated Jul. 1, 2008.
Office Action (Application No. 08002060.5) dated Apr. 1, 2010.

* cited by examiner

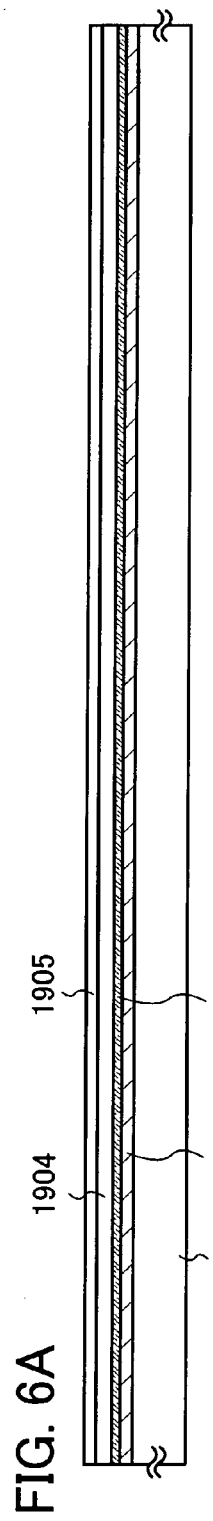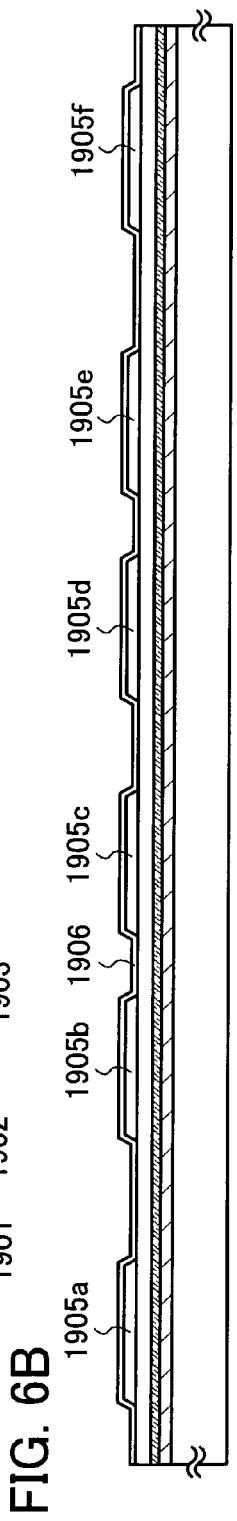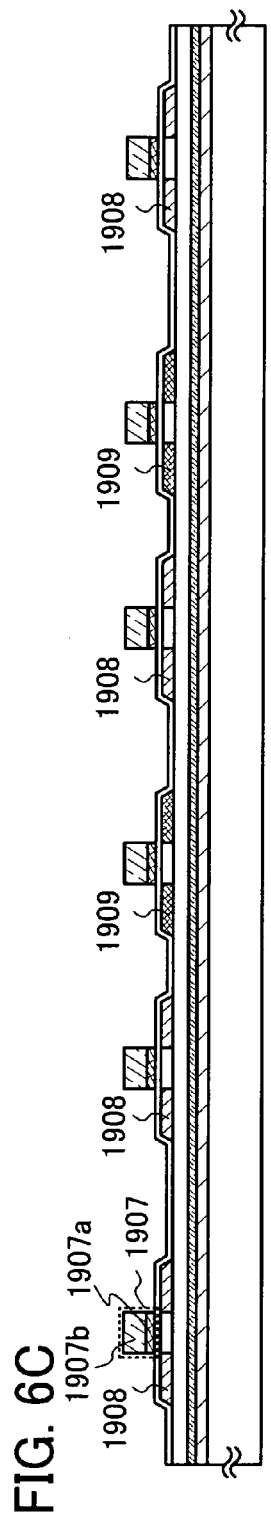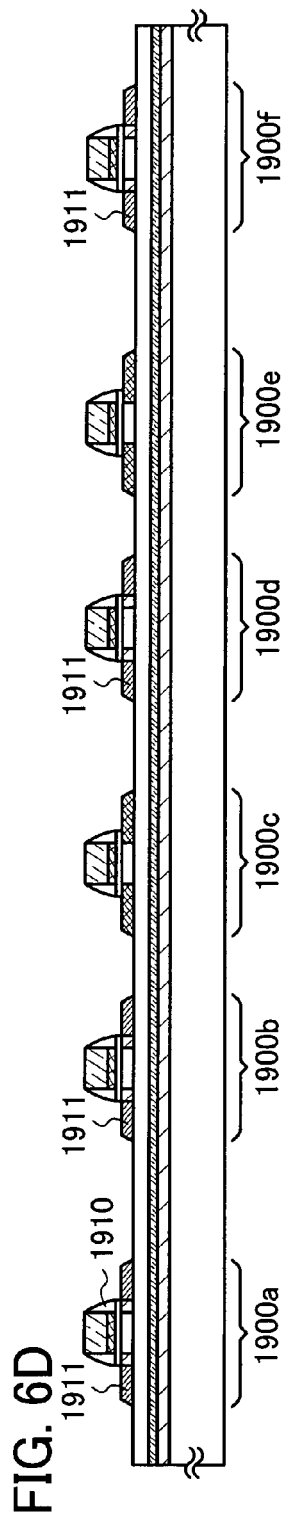

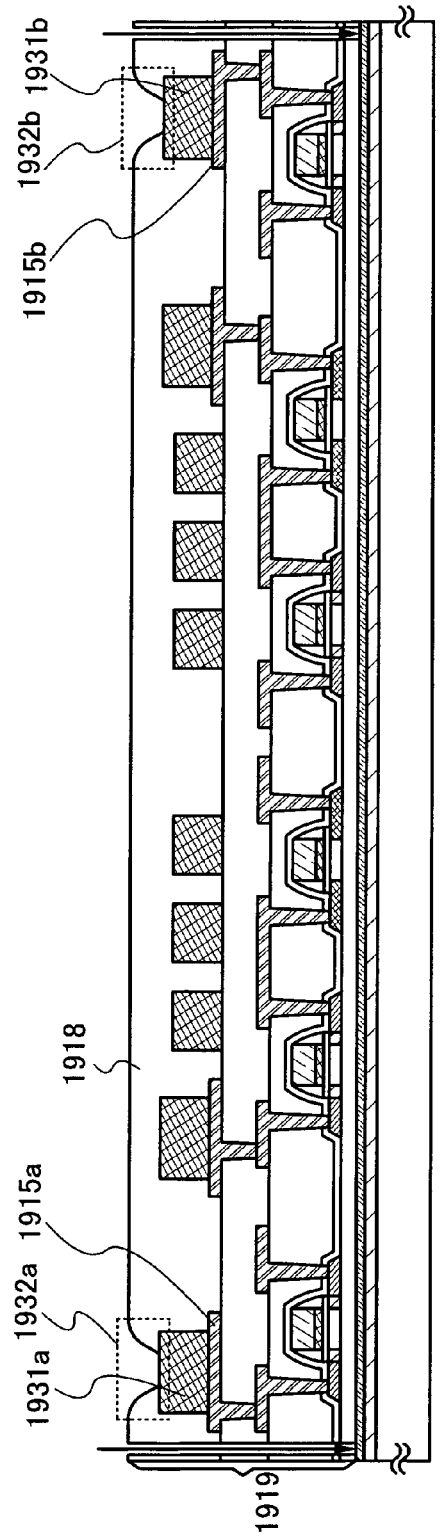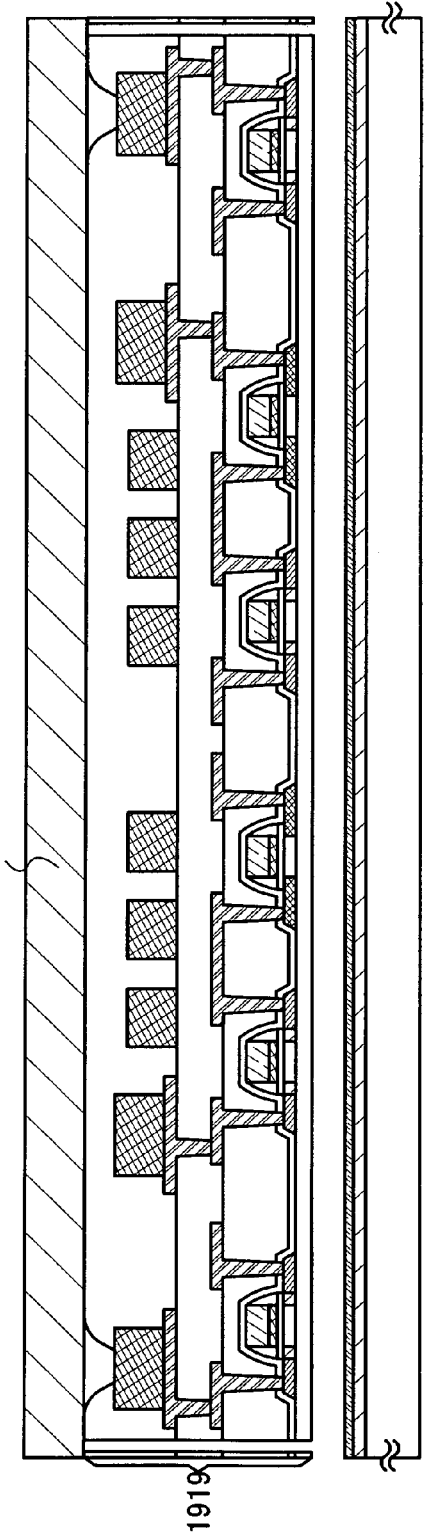

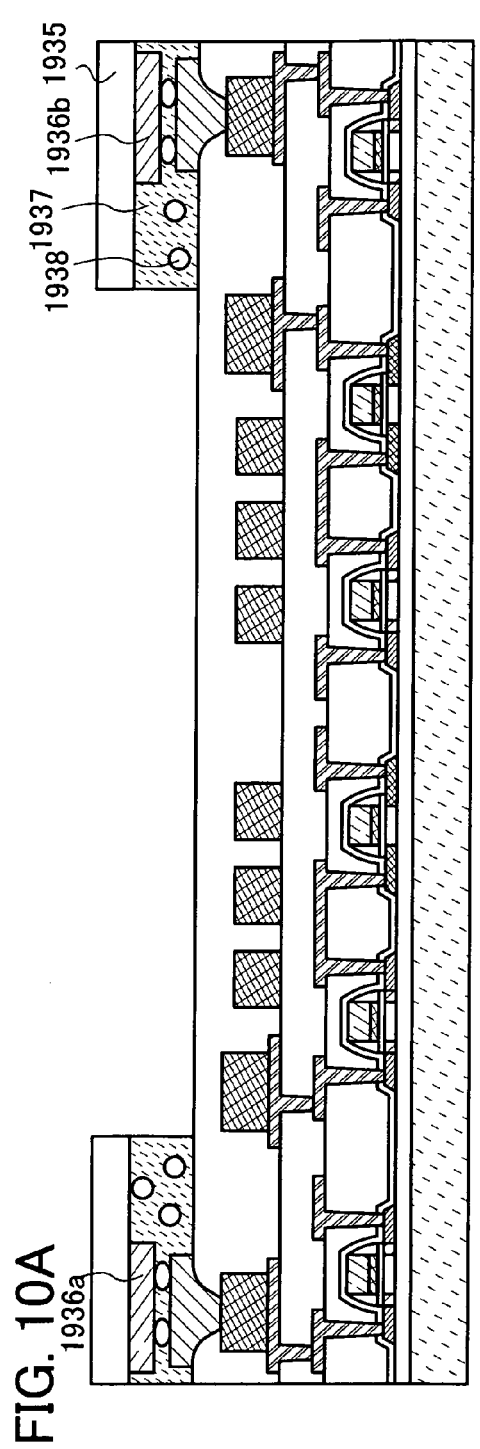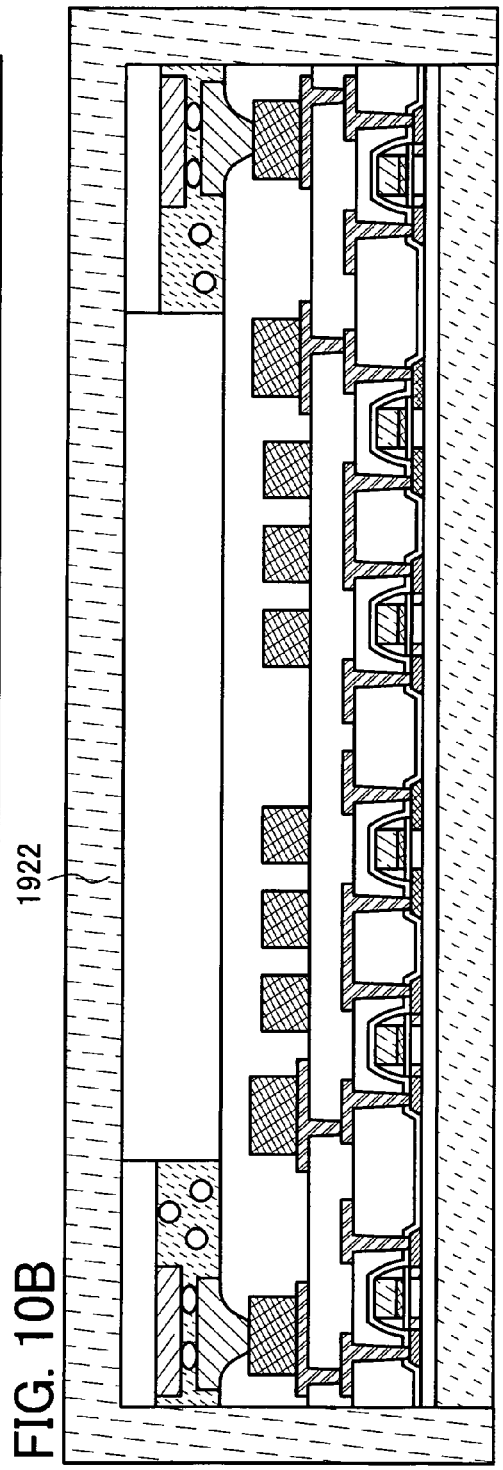

ASSIST DEVICE

BACKGROUND OF THE INVENTION

1. Field of the Invention

The present invention relates to an assist device which detects a biosignal such as a myoelectric potential, pressure, or a neurotransmitter, and substitutes for or assists any of functions of extremities.

2. Description of the Related Art

Conventionally, there has been an artificial limb as a device which assists functions of an amputated extremity. In addition, there has been an assist device which can perform remotely control a driving portion working with human intention in circumstances where human operations are difficult.

Research has been made on a conventional artificial limb which just compensates appearance to have a motor function. For example, there is a myoelectric hand. A myoelectric potential at the time of moving a muscle is sensed at a skin surface and change in the myoelectric potential is used as a signal, so that the artificial hand can be moved (see Reference 1: Japanese Published Patent Application No. 2006-239447; Reference 2: Japanese Published Patent Application No. 2005-334675; and Reference 3: Japanese Published Patent Application No. H11-113866).

SUMMARY OF THE INVENTION

However, high voltage is necessary for driving an artificial hand and there has been a risk that high voltage would flow into a human body when an electrode which detects a myoelectric potential and a portion which drives the artificial hand are electrically connected. In addition, in the case of remotely controlling a device working with human intention, when an operating portion of a human and the device working with the human intention are connected by a cable or the like, there is a risk that high voltage would flow into a human body, many cables are necessary, and operations are complicated and limited.

In view of the foregoing problems, the present invention provides a higher-performance assist device which is safer.

An assist device of the present invention includes a detecting portion and an assist device driving portion. The detecting portion includes a first sensor, a first transmitting/receiving circuit, a first data processing circuit, a first charging circuit, and a first battery. The assist device driving portion includes a driving portion, a second data processing circuit, a second transmitting/receiving circuit, a second charging circuit, and a second battery. In addition, in the assist device of the present invention, electromagnetic waves are transmitted from the second transmitting/receiving circuit provided in the assist device driving portion, and the first transmitting/receiving circuit provided in the detecting portion receives the electromagnetic waves. Induced electromotive force generated at that time is input to the first charging circuit through the first data processing circuit provided in the detecting portion, so that the first battery provided in the detecting portion is charged. In this specification, these functions are collectively referred to as a wireless charging means. Further, in the assist device of the present invention, electromagnetic waves of biological information detected by the first sensor are transmitted from the first transmitting/receiving circuit provided in the detecting portion. The second transmitting/receiving circuit of the assist device driving portion receives the electromagnetic waves, signals are processed by the second data processing circuit, and the driving portion provided in the assist device driving portion is operated based on the processed signals.

Here, the first data processing circuit includes an amplifier circuit, an A/D converter circuit, and a first central arithmetic processing circuit. The second data processing circuit includes a drive control circuit, a second sensor, and a second central arithmetic processing circuit.

In addition, the first sensor provided in the detecting portion is a sensor which detects biological information. Typically, a myoelectric potential electrode detecting a myoelectric potential and a reference electrode can be used. Alternatively, a neural potential detecting element which detects a neural potential can be used. Further alternatively, a sensor which detects displacement of movement of a tendon, pressure generated on a surface of a muscle, speed, or an angle, or the like can be used. As the sensor which detects displacement, a pressure sensor, an acceleration sensor, an angular velocity sensor, or a bending resistor can be used.

Here, the detecting portion can be embedded inside of an excised extremity. In addition, the detecting portion can be put on the outside of the body so that the detecting portion is wrapped around a portion detecting a biosignal.

The assist device driving portion is fixed to an edge of the excised extremity. Alternatively, the assist device driving portion may be a driving portion of an assist device for remote control.

In addition, each of the first transmitting/receiving circuit provided in the detecting portion and the second transmitting/receiving circuit provided in the assist device driving portion includes a demodulation circuit, a decoding circuit, a logic arithmetic control circuit, a memory circuit, an encoding circuit, and a modulation circuit. Further, the first charging circuit includes a rectifier circuit inputting induced electromotive force generated in an antenna provided in the first transmitting/receiving circuit, a current-voltage control circuit, and a charge control circuit. The second charging circuit provided in the assist device driving portion includes a rectifier circuit inputting external power supply voltage, a current-voltage control circuit, and a charge control circuit.

Further, in the assist device of the present invention, the first sensor included in the detecting portion is connected to the amplifier circuit. The amplifier circuit is connected to the A/D converter circuit. The A/D converter circuit is connected to the first central arithmetic processing circuit provided in the detecting portion. The first transmitting/receiving circuit provided in the detecting portion is connected to the first central arithmetic processing circuit provided in the detecting portion and the first charging circuit provided in the detecting portion. The first charging circuit provided in the detecting portion is connected to the first battery. The first battery provided in the detecting portion supplies power to the inside of the detecting portion.

Moreover, the second central arithmetic processing circuit provided in the assist device driving portion is connected to the drive control circuit and the second sensor. The drive control circuit is connected to the driving portion. The second transmitting/receiving circuit provided in the assist device driving portion is connected to the second central arithmetic processing circuit provided in the assist device driving portion and the second charging circuit provided in the assist device driving portion. The second charging circuit provided in the assist device driving portion is connected to the second battery provided in the assist device driving portion. The second battery provided in the assist device driving portion supplies power to the inside of the assist device driving portion.

When the wireless charging means is used for the detecting portion, the assist device driving portion which has a high voltage portion and the detecting portion which is in contact with a human body are electrically separated, so that safety at the time of using the assist device is improved.

When communication between the detecting portion and the assist device driving portion is performed wirelessly, a connection terminal is not necessary, so that the driving portion of the assist device can be easily changed. In addition, in the case where the assist device is an artificial limb, the artificial limb fixed to a stump can be easily changed.

When communication between the detecting portion and the assist device driving portion is performed wirelessly, the assist device can be remotely controlled. Thus, when the assist device of the present invention is utilized in order to perform risky operations, operations in circumstances where human operations are difficult, e.g., in particular circumstances such as outer space and deep ocean, the assist device can be operated in a safe place for a human body, so that safety of the human body can be maintained.

BRIEF DESCRIPTION OF THE DRAWINGS

In the accompanying drawings:

FIGS. 6A to 6D illustrate manufacturing steps of an assist device of the present invention;

FIGS. 8A and 8B illustrate manufacturing steps of an assist device of the present invention;

FIGS. 10A and 10B illustrate manufacturing steps of an assist device of the present invention;

DETAILED DESCRIPTION OF THE INVENTION

Figure 1:
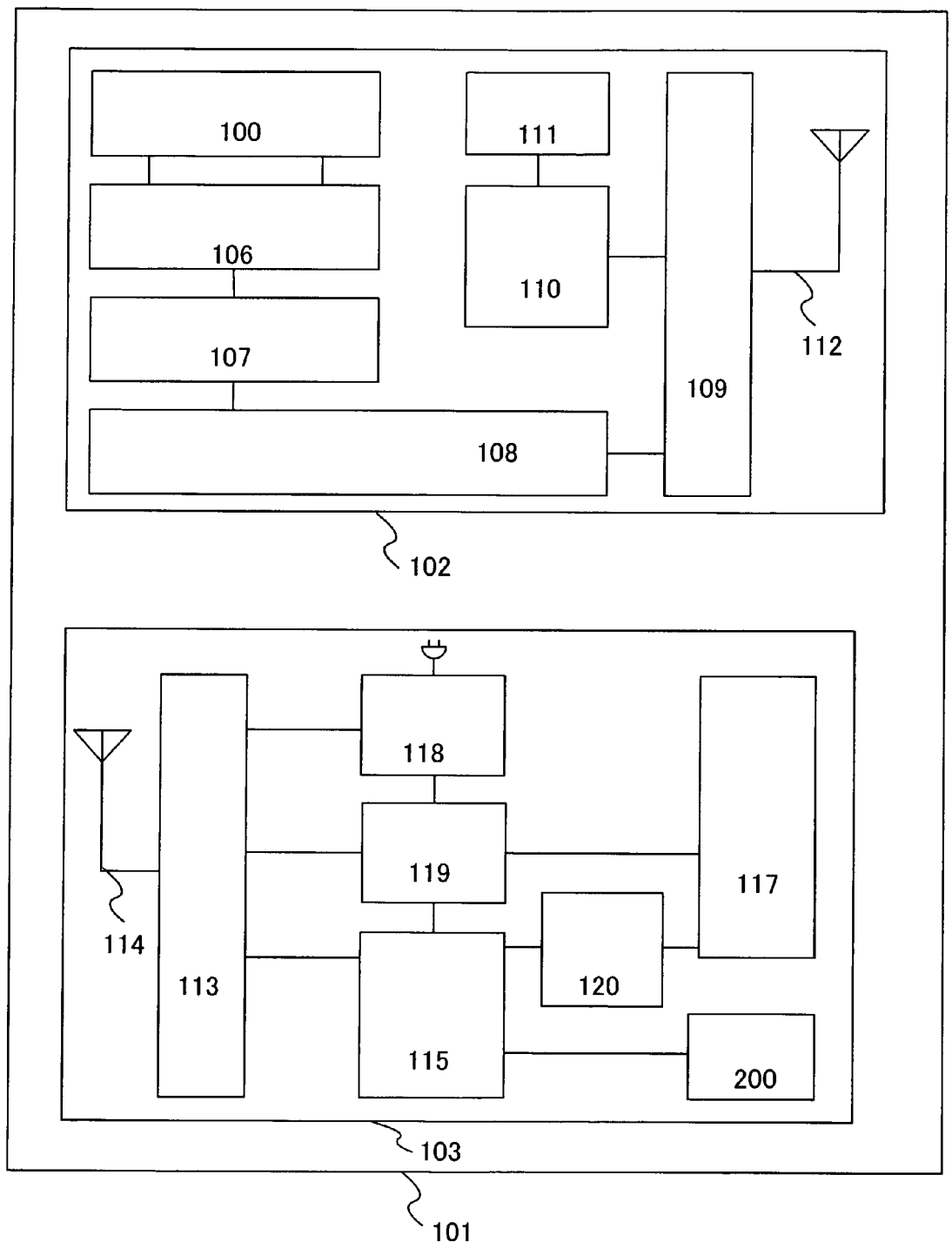
FIG. 1 illustrates a structure of an assist device of the present invention.

Hereinafter, embodiment modes of the present invention will be described with reference to the drawings. Note that the present invention is not limited to the following description. The present invention can be implemented in various different ways and it will be readily appreciated by those skilled in the art that various changes and modifications are possible without departing from the spirit and the scope of the present invention. Therefore, the present invention should not be construed as being limited to the following description of the embodiment modes. Note that as structures of the present invention are described with reference to the drawings, the like portions are denoted by common reference numerals in different drawings.

Embodiment Mode 1

In this embodiment mode, structures and operations of an assist device of the present invention are described.

As shown in FIG. 1, an assist device 101 of the present invention includes a detecting portion 102 and an assist device driving portion 103.

First, each part of the detecting portion 102 is described. The detecting portion 102 includes a first sensor 100 which detects a biosignal, an amplifier circuit 106 which amplifies the detected biosignal, an A/D converter circuit 107 which converts the amplified signal into a digital signal, a central arithmetic processing circuit 108 which processes the signal, a transmitting/receiving circuit 109 for communicating with the assist device driving portion, an antenna 112, a battery 111 for driving these circuits, and a charging circuit 110 for charging the battery 111.

As a method for fixing the detecting portion 102 to a human body, the following can be used: embedding the detecting portion 102 in the body, putting the detecting portion 102 on the outside of the body so that detecting portion 102 is wrapped around a portion detecting a biosignal, incorporating the detecting portion 102 in a socket which connects the assist device driving portion 103 and the human body, and the like. Note that the method for fixing the detecting portion 102 is not limited to the above-described modes.

In the case of using the implantable detecting portion 102, it is preferable that each of the amplifier circuit 106, the A/D converter circuit 107, the central arithmetic processing circuit 108, the transmitting/receiving circuit 109, the antenna 112, the battery 111, and the charging circuit 110 is thin and soft like a film and the implantable detecting portion 102 be covered with a material which is safe of the human body, such as silicon. In addition, a material which is safe of the human body such as titanium, platinum, or gold is preferably used as a metal which is necessary to be exposed to the detecting portion 102. Accordingly, the detecting portion 102 can be permanently put in the body.

When the detecting portion 102 is formed using any of the above-described materials, the assist device driving portion 103 can be easily changed in accordance with growth stages or applications. In addition, since a junction between the detecting portion 102 and the assist device driving portion 103 is separated at a skin surface and data can be transmitted without using a connection terminal or the like, a connection terminal is not exposed and bathing, swimming, and wet work taking off the assist device driving portion 103 can be performed. Further, when a connection terminal is not exposed to the skin surface, corrosion, electric leakage, and the like can be prevented and there are advantages in beauty, infection prevention, and the like.

The first sensor 100 is preferably provided at a position where the first sensor 100 can easily detect a biosignal which is to be detected.

As a biosignal which is to be detected for controlling the assist device driving portion 103, there are one or more of a myoelectric potential, a neural potential generated in accordance with an instruction to "move a certain portion of the body" which is issued from the brain, change in movement of a muscle or a tendon, pressure generated on a skin surface or in the body, speed, and an angle, and the like.

In order to detect a myoelectric potential, a myoelectric potential electrode is used for the first sensor 100. Alternatively, in order to detect a neural potential, a neural potential detecting element is used for the first sensor 100. Further alternatively, in order to detect displacement of movement of a tendon, pressure generated on a surface of a muscle, speed, or an angle, or the like, a sensor which detects displacement is used for the first sensor 100. Typical examples of the sensor which detects displacement are a pressure sensor, an acceleration sensor, an angular velocity sensor, and a bending resistor. Since a weak signal can also be detected by using a MEMS for the sensor which detects displacement, the sensor which detects displacement is small and has high sensitivity.

When a signal detected by the first sensor 100 is input to the amplifier circuit 106, the amplifier circuit 106 amplifies the signal to a potential which is suitable for signal processing. Generally, the amplifier circuit 106 is formed using a circuit using differential amplification.

The A/D converter circuit 107 is a circuit which converts a signal generated by the amplifier circuit 106 into a digital signal which can be used in the central arithmetic processing circuit 108.

The central arithmetic processing circuit 108 provided in the detecting portion 102 performs pattern recognition based on a plurality of A/D converted digital signals; determines a series of operations of a joint included in the assist device driving portion 103, such as flection, extension, pronation, supination, abduction, and adduction, which is necessary for the user; and outputs a digital signal corresponding to the operation. Note that in order to realize a plurality of joint operations at the same time in the assist device driving portion 103, it is preferable that a signal having a plurality of channels be output at the same time. In addition, pattern recognition may be performed using a central arithmetic processing circuit 115 provided in the assist device driving portion 103. In this case, the central arithmetic processing circuit 108 provided in the detecting portion 102 is not necessary.

Since the first sensor 100, the amplifier circuit 106, the A/D converter circuit 107, the central arithmetic processing circuit 108 provided in the detecting portion 102, the transmitting/receiving circuit 109, and the charging circuit 110 can be made smaller by being integrated and using CMOS transistor technology, they are suitable for being embedded in the body. When an n-channel thin film transistor and a p-channel thin film transistor are used for a CMOS transistor, the detecting portion 102 can be thinned, which is preferable.

Figure 4A:
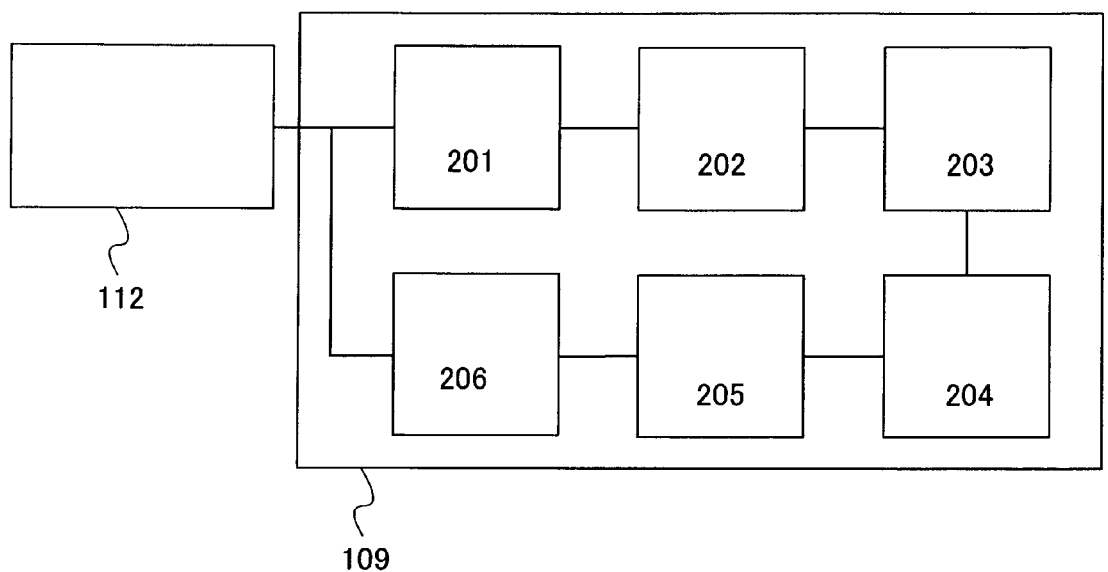
FIGS. 4A and 4B illustrate a transmitting/receiving circuit and a charging circuit which are included in a myoelectric artificial limb of the present invention.

As shown in FIG. 4A, the transmitting/receiving circuit 109 provided in the detecting portion 102 includes circuits for wireless communication, such as a demodulation circuit 201, a decoding circuit 202, a logic arithmetic control circuit (a logic circuit) 203, a memory circuit 204, an encoding circuit 205, and a modulation circuit 206, and wirelessly communicates with the assist device driving portion 103.

Further, the transmitting/receiving circuit 109 provided in the detecting portion 102 includes a transmitting portion which transmits a signal having a single channel or a plurality of channels to the transmitting/receiving circuit 113 provided in the assist device driving portion 103, a receiving portion which receives an electromagnetic wave or an electric field from the transmitting/receiving circuit 113 provided in the assist device driving portion 103 and outputs it to the charging circuit 110, and the like.

As one mode, the transmitting portion performs phase shift keying of a digital signal having a plurality of channels and transmits the digital signal having the plurality of channels to the antenna 114 provided in the assist device driving portion 103 through the antenna 112 provided in the detecting portion 102 by an electromagnetic wave using orthogonal frequency division multiplexing. As another mode, the transmitting portion can transmit digital signals using a coiled antenna for channels which are necessary for communication by an electromagnetic induction method. In addition, the transmitting portion can also performs optical communication. When the detecting portion 102 and the assist device driving portion 103 are electrically separated as described above, safety of the user can be improved. In the case of using optical communication, communication can be performed through a skin using an infrared ray or the like. In this case, a transmitting/receiving circuit provided in a myoelectric potential detecting portion is preferably provided close under the skin.

For the antenna 112 provided in the detecting portion 102, a transmission antenna and a reception antenna may be separately provided. Alternatively, the antenna 112 provided in the detecting portion 102 can perform transmission and reception using one antenna. In addition, the antenna may be mounted inside or on a surface of the detecting portion 102, or can be separately provided outside. Further, in the case where an electromagnetic induction method is used for communication with the assist device driving portion 103, a coiled antenna for channels which are necessary for transmission and reception of data can be provided. In the case of performing optical communication, a light-emitting portion and a light-receiving portion for transmitting and receiving a signal for driving the assist device driving portion 103 are provided as well as a reception antenna for receiving an electromagnetic wave for generating power.

Figure 4B:
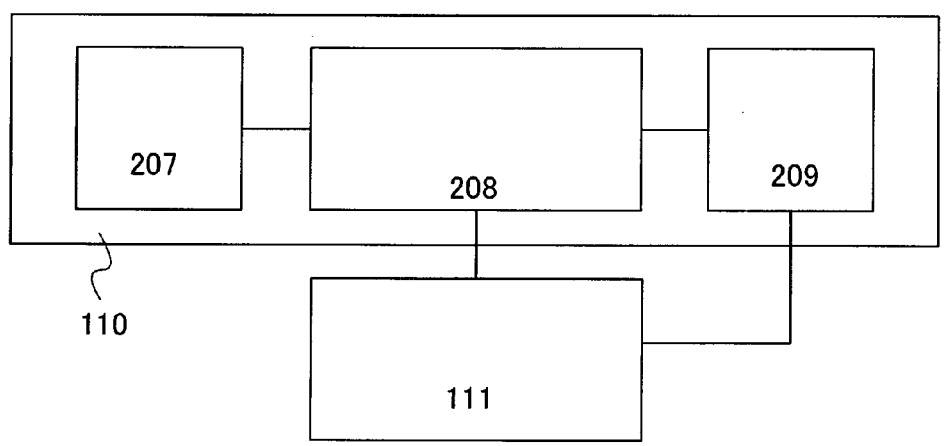

The charging circuit 110 provided in the detecting portion 102 includes a rectifier circuit 207 which converts input AC current into DC current, a current-voltage control circuit (also referred to as a regulator) 208 which makes rectified power into voltage suitable for charging, a charging control circuit 209 which controls voltage output to the battery 111, and the like (see FIG. 4B).

Here, in the case of embedding the detecting portion 102 in the body, in order to reduce a burden on the body to be embedded with the detecting portion 102, it is preferable that the detecting portion 102 be as small as possible. One of elements which determine the size of the detecting portion 102 is the battery 111. Since the battery 111 can be made smaller as power consumption of the detecting portion 102 is lower, a structure in which the number of signal processing performed by the central arithmetic processing circuit 108 provided in the detecting portion 102 is reduced and necessary signal processing is performed by the central arithmetic processing circuit 115 provided in the assist device driving portion 103 can be used, for example. Alternatively, a method can be employed in which the battery 111 of the detecting portion 102 is made smaller and charging is frequently performed at short time intervals.

In the case where the user takes off the assist device driving portion 103, the assist device preferably has a function of saving power by stopping the detecting portion 102. In order to realize this function, a structure can be used in which an instruction to stop operations of the detecting portion 102 or an instruction to stop operations of the detecting portion 102 from the assist device detecting portion 103 can be given by determining whether the transmitting/receiving circuit 109 included in the detecting portion 102 and the transmitting/receiving circuit 113 included in the assist device driving portion 103 are in the range of a distance where communication can be performed.

The transmitting/receiving circuit 109 of the detecting portion 102 receives an electromagnetic wave transmitted from the antenna 114 provided in the assist device driving portion 103 through the antenna 112 provided in the detecting portion 102, and outputs obtained AC current to the charging circuit 110. For example, as one mode, a structure can be used in which displacement current which is obtained by receiving change in magnetic flux generated from a coiled antenna provided in the assist device driving portion 103 by a coiled antenna provided in the detecting portion 102 is output to the charging circuit 110. Note that the present invention is not limited to this mode.

When the assist device 101 of the present invention includes the transmitting/receiving circuits for wireless communication and the wireless charging means (an RF battery) as described above, the assist device driving portion 103 and the detecting portion 102 can be electrically separated. In addition, conductive part of the detecting portion 102 can be made not to be exposed. Therefore, the assist device 101 of the present invention can be an assist device which is safe for the user and is water-resistant.

Here, a rechargeable secondary battery can be used for the battery 111 provided in the detecting portion 102. For example, an electric-double layer capacitor having a collector electrode, a polarizable electrode, a separator, or an electrolytic solution can be used. In the case of using the battery 111 provided in the detecting portion 102 embedded in the body, an electrolytic solution and an electrode which are safe for the human body is preferably selected.

Next, the assist device driving portion 103 is described in detail. The assist device driving portion 103 includes a driving portion 117 for operations, a drive control circuit 120 for driving and controlling the driving portion 117, a second sensor 200 for detecting pressure, temperature, or the like, a central arithmetic processing circuit 115 which processes a driving control signal, a signal from the sensor, or the like, a transmitting/receiving circuit 113 for receiving a signal from the detecting portion 102 and transmitting an electromagnetic wave or a magnetic flux for charging to the detecting portion 102, a battery 119 for driving the assist device driving portion 103, and a charging circuit 118 for charging the battery 119.

The assist device driving portion 103 transmits power of the battery 119 wirelessly through the transmitting/receiving circuit 113. Therefore, the transmitting/receiving 113 preferably includes an oscillator for transmitting power in addition to the structure of the transmitting/receiving circuit 109 of the detecting portion 102.

In addition, the assist device driving portion 103 includes a cover which entirely covers the assist device driving portion 103. The assist device driving portion 103 is connected to the assist device or the user by a socket using silicon. Alternatively, the assist device driving portion 103 is fixed by a known method, for example, by fixing the assist device driving portion 103 to the assist device or the user using a band.

The driving portion 117 includes a driving mechanism having a skeleton and a joint, a wire, a sleeve, a motor for pressing and pulling the wire, an artificial muscle, and the like.

A signal from the central arithmetic processing circuit 115 provided in the assist device driving portion 103 is input to the drive control circuit 120, and current and voltage which are necessary for operations of the motor or the artificial muscle of the driving portion 117 are generated.

The second sensor 200 detecting pressure and temperature which are external stimuli may be provided on a surface of the assist device driving portion 103.

For example, a temperature sensor can detect temperature of an object which is touched by the assist device driving portion 103.

In a risky condition for using the assist device, such as high temperature, a structure can also be used in which the risky condition of the assist device can be known by using warning indication using light or sound. Note that depending on applications of the assist device, a structure without a temperature sensor can be used.

Alternatively, when a pressure sensor is provided, pressure applied to the assist device driving portion 103 can be detected.

For such a temperature sensor, a pressure sensor, or the like, a sensor which is formed using MEMS (micro electro mechanical system) technology can be used, for example. A sensor which is formed using MEMS technology is small, lightweight, and highly-sensitive. Therefore, weight of the assist device driving portion 103 can be reduced and movement of the assist device can be approximated to movement of real extremities.

The transmitting/receiving circuit 113 provided in the assist device driving portion 103 includes a transmitting portion which transmits an electromagnetic wave or an electric field to the detecting portion 102, and a receiving portion which receives and demodulates the electromagnetic wave, the electric field, or light transmitted from the detecting portion 102, decodes the electromagnetic wave, the electric field, or light transmitted from the detecting portion 102 into a digital signal, and outputs the digital signal.

As a specific structure, for example, the transmitting/receiving circuit 113 provided in the assist device driving portion 103 includes circuits for wireless communication, such as a demodulation circuit, a decoding circuit, a logic arithmetic control circuit (a logic circuit), a memory circuit, an encoding circuit, and a modulation circuit, and wirelessly communicates with the detecting portion 102.

The transmitting portion of the transmitting/receiving circuit 113 transmits an electromagnetic wave using an antenna in order to charge the battery 111 of the detecting portion 102. For example, the transmitting portion of the transmitting/receiving circuit 113 can transmit power using a coiled antenna by an electromagnetic induction method. Note that the present invention is not limited to this mode, and a dipole antenna, a patch antenna, or the like can be used by a radio wave method.

As one mode, the receiving portion of the transmitting/receiving circuit 113 can have a structure in which phase shift keying and decoding of a transmitted signal are performed using orthogonal frequency division multiplexing, and the signal is output to the central arithmetic processing circuit 115 as a digital signal having a plurality of channels. Alternatively, the receiving portion of the transmitting/receiving circuit 113 can have a structure in which demodulation and decoding of a transmitted signal are performed using a coiled antenna for channels which are necessary for communication by an electromagnetic induction method, and a digital signal having a plurality of channels is output to the central arithmetic processing circuit 115. Further alternatively, the receiving portion of the transmitting/receiving circuit 113 can have a structure in which demodulation and decoding of an optical signal are performed, and a digital signal having a plurality of channels is output to the central arithmetic processing circuit 115. Note that the assist device of the present invention is not limited to such a mode, and can have a structure in which the assist device driving portion 103 and the detecting portion 102 communicate with each other using various methods.

Data on a biosignal which is transmitted from the detecting portion 102 and is received by the transmitting/receiving circuit 113 provided in the assist device driving portion 103 is input to the central arithmetic processing circuit 115 provided in the assist device driving portion 103; the central arithmetic processing circuit 115 provided in the assist device driving portion 103 performs pattern recognition based on this data;

and the central arithmetic processing circuit 115 provided in the assist device driving portion 103 determines a series of operations of a joint included in the assist device driving portion 103, such as flection, extension, pronation, supination, abduction, and adduction, which is necessary for the user.

Note that in the case of performing pattern recognition by the central arithmetic processing circuit 108 provided in the detecting portion 102, for example, pattern recognition in the central arithmetic processing circuit 115 provided in the assist device driving portion 103 is not necessary.

When the necessary operations are determined by data processing as described above, in order to operate a motor or an artificial muscle corresponding to the operations, a signal is output to the drive control circuit 120.

In addition, the arithmetic processing circuit 115 provided in the assist device driving portion 103 may have a learning function of pattern recognition. For example, the arithmetic processing circuit 115 provided in the assist device driving portion 103 can have a function of learning based on the amount and an operation result of a biosignal input to the detecting portion 102, and determining a parameter which is suitable for the user of the assist device 101 to perform operations.

The charging circuit 118 provided in the assist device driving portion 103 includes a rectifier circuit which converts AC current input from an external power supply into DC current, a current-voltage control circuit for making rectified power into a suitable value for charging, a charging control circuit which controls power supplied to the battery 119, and the like. The power input from the external power supply is stored in the battery 119 through the charging circuit 118. The battery 119 which is charged as described above supplies power to each part of the assist device driving portion 103 in order to drive the whole assist device driving portion 103.

The battery 119 provided in the assist device driving portion 103 can also have a structure in which an electromagnetic wave which is transmitted from an external charger is received through the antenna 114 provided in the assist device driving portion 103, obtained AC current is output to the charging circuit 118 provided in the assist device driving portion 103 to change the battery 119 provided in the assist device driving portion 103. Specifically, a structure can be used in which displacement current which is obtained by receiving change in magnetic flux generated from a coiled antenna included in the external charger by the coiled antenna provided in the assist device driving portion 103 is output to the charging circuit 118 provided in the assist device driving portion 103.

Here, the assist device driving portion 103 needs high power because it includes the driving portion 117 which includes the motor, the artificial muscle, or the like. However, it is preferable that the battery 119 provided in the assist device driving portion 103 be as lightweight as possible.

In addition, even in the case where power is supplied to the assist device driving portion 103 from outside using an outlet, it is preferable to provide a cover so that the assist device driving portion 103 is water-resistant to some extent, such as covering the assist device driving portion 103 with a cover having rubber packing after unplugging the outlet.

When the assist device 101 is water-resistant as described above, danger of an electric shock or electric leakage is removed and quality of life of the user can be improved.

Note that a battery which is similar to the battery 111 of the detecting portion 102 can be used for the battery 119. When a wireless charging means (an RF battery) is employed for the detecting portion 102 as described in this embodiment mode, the assist device driving portion 103 which has a high voltage portion and the detecting portion 102 which is in contact with a human body are electrically separated, so that the assist device which has high security can be provided. Further, in this embodiment mode, since a connection terminal is not necessary by performing communication between the detecting portion 102 and the assist device driving portion 103 wirelessly, the assist device 101 which can be easily changed in accordance with growth stages or necessity can be provided.

Embodiment Mode 2

In this embodiment mode, structures and operations of a myoelectric artificial limb are described as a typical mode of an assist device of the present invention.

Figure 2:
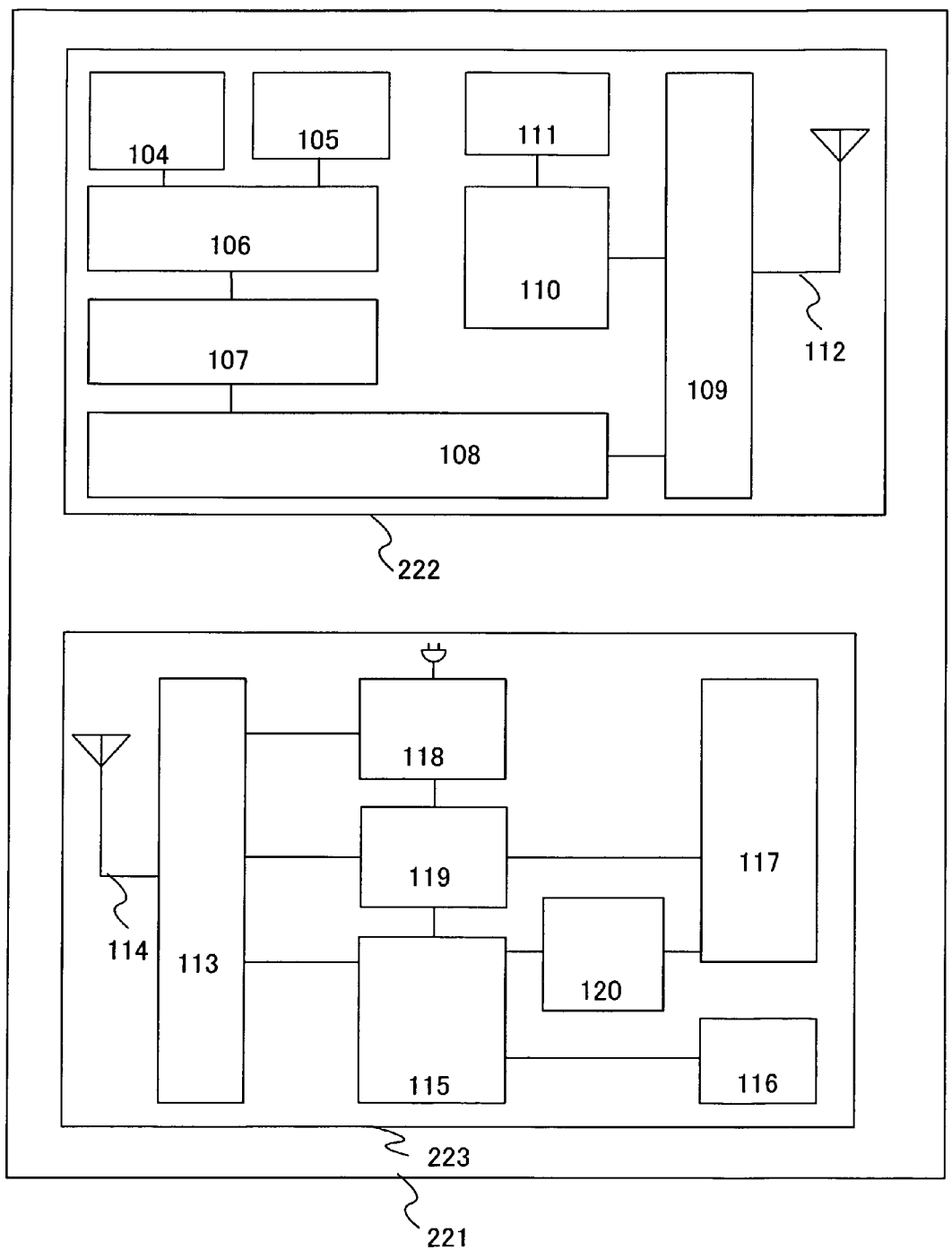
FIG. 2 illustrates a structure of an assist device of the present invention.

As shown in FIG. 2, a myoelectric artificial limb 221 of the present invention includes a myoelectric potential detecting portion 222 and an artificial limb driving portion 223.

First, each part of the myoelectric potential detecting portion 222 is described. The myoelectric potential detecting portion 222 includes a myoelectric potential electrode 104 which detects a myoelectric potential, a reference electrode 105 which detects noise other than the myoelectric potential, the amplifier circuit 106 which amplifies the detected myoelectric potential, the A/D converter circuit 107 which converts the amplified signal into a digital signal, the central arithmetic processing circuit 108 which processes the signal, the transmitting/receiving circuit 109 for communicating with the artificial limb driving portion, the antenna 112, the battery 111 for driving the circuits, and the charging circuit 110 for charging the battery.

Figure 3:
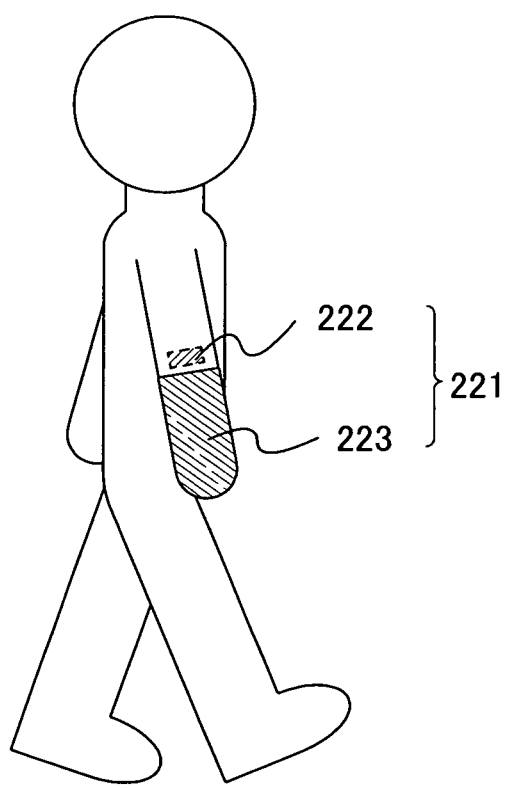
FIG. 3 illustrates an application of an assist device of the present invention.

As a method for fixing the myoelectric potential detecting portion 222 to a human body, the following can be used: embedding the myoelectric potential detecting portion 222 in the body, putting the myoelectric potential detecting portion 222 on the outside of the body so that the myoelectric potential detecting portion 222 is wrapped around a portion detecting a myoelectric potential, incorporating the myoelectric potential detecting portion 222 in a socket which connects the artificial limb driving portion 223 and the body, and the like. Note that the method for fixing the myoelectric potential detecting portion 222 is not limited to this mode. In this embodiment mode, a mode is described in which the myoelectric potential detecting portion 222 is embedded close to a nerve or a muscle in a body of part (a stump) to which the artificial limb driving portion 223 is connected. FIG. 3 shows an example in which the artificial limb driving portion 223 is embedded in an arm amputated at a forearm portion.

When the myoelectric potential detecting portion 222 is embedded in the human body, a myoelectric potential is detected without involving a skin, and data processing of the detected signal is performed, even a small signal can be detected with high accuracy and a more complicated artificial limb can be controlled.

When the myoelectric potential detecting portion 222 is attached to the body, in the case of detecting a myoelectric potential on a skin surface, the detected myoelectric potential corresponds to a myoelectric potential obtained by overlapping myoelectric potentials generated by a plurality of muscles which are close to the skin. However, in the case of embedding the myoelectric potential detecting portion 222 in the body, a myoelectric potential of a particular muscle can be detected, and there is a possibility that complicated and flexible movement of the artificial limb can be realized by comprehensively judging pieces of data on respective muscles.

In the case of detecting a myoelectric potential from the skin surface, a polarized potential generated between a myoelectric potential electrode attached to the skin surface and an electrolyte such as sweat on the skin, or noise caused by vibration of an electrode wiring, or a fluorescent lamp, a home electric appliance, a machine tool, or the like which is around the electrode is mixed, which is inevitable.

In the case of detecting a myoelectric potential using the embedded myoelectric potential electrode 104 as described above, there are an advantageous effect of suppressing detection of unnecessary data other than such a myoelectric potential, and a possibility that the myoelectric potential can be detected with higher accuracy.

In the case of using the implantable myoelectric potential detecting portion 222, it is preferable that each of the amplifier circuit 106, the A/D converter circuit 107, the central arithmetic processing circuit 108, the transmitting/receiving circuit 109, the antenna 112, the battery 111, and the charging circuit 110 is thin and soft like a film and the implantable myoelectric potential detecting portion 222 be covered with a material which is safe for the human body, such as silicon. In addition, a material which is safe for the human body such as titanium, platinum, or gold can be used as a metal which is necessary to be exposed to the myoelectric potential detecting portion 222. Accordingly, the myoelectric potential detecting portion 222 can be permanently put in the body.

When the myoelectric potential detecting portion 222 is formed using any of the above-described materials, the artificial limb driving portion 223 can be easily changed in accordance with growth stages or applications. In addition, since a terminal or the like is not exposed to the skin surface, bathing, swimming, and wet work taking off the artificial limb driving portion 223 can be performed. Further, when a terminal or the like is not exposed to the skin surface, corrosion, electric leakage, and the like can be prevented and there are advantages in beauty, infection prevention, and the like.

The myoelectric potential electrode 104 is preferably provided in a belly muscle which is close to a tendon of a muscle. This is because a myoelectric potential is generated from the central of a muscle toward tendons at opposite ends.

The reference electrode 105 has a function of removing noise or a signal which is mixed into a myoelectric potential detected by the myoelectric potential electrode 104. Since it is necessary to detect an object which is similar to such a signal or noise adversely affecting detection of a myoelectric potential by the reference electrode 105, the reference electrode 105 is preferably provided near a muscle which is to be detected and in a joint, a tendon, or the like which has less influence by the myoelectric potential.

Circuits which are similar to those of Embodiment Mode 1 can be used for the amplifier circuit 106, the A/D converter circuit 107, the central arithmetic processing circuit 108 provided in the myoelectric potential detecting portion 222, the transmitting/receiving circuit 109, and the charging circuit 110. Since the amplifier circuit 106, the A/D converter circuit 107, and the central arithmetic processing circuit 108 provided in the myoelectric potential detecting portion 222, can be made smaller by being integrated and using CMOS transistor technology, they are suitable for being embedded in the body. When an n-channel thin film transistor and a p-channel thin film transistor are used for a CMOS transistor, the myoelectric potential detecting portion 222 can be thinned, which is preferable.

When the myoelectric potential detecting portion 222 and the artificial limb driving portion 223 are electrically separated as described above, safety of the user can be improved.

For the antenna 112 provided in the myoelectric potential detecting portion 222, a transmission antenna and a reception antenna may be separately provided. Alternatively, the antenna 112 provided in the myoelectric potential detecting portion 222 can perform transmission and reception using one antenna. In addition, the antenna may be mounted inside or on a surface of the myoelectric potential detecting portion 222, or can be separately provided outside. Further, in the case where an electromagnetic induction method is used for communication with the artificial limb driving portion 223, a coiled antenna for channels which are necessary for transmission and reception of data can be provided. In the case of performing optical communication, a reception antenna for receiving a radio wave for power is provided.

Circuits which are similar to the charging circuit 110 and the transmitting/receiving circuit 109 described in Embodiment Mode 1 can be used for the charging circuit 110 and the transmitting/receiving circuit 109 provided in the myoelectric potential detecting portion 222.

When the myoelectric artificial limb 221 of the present invention includes the transmitting/receiving circuits for wireless communication and the wireless charging means (an RF battery) as described above, the artificial limb driving portion 223 and the myoelectric potential detecting portion 222 can be electrically separated. In addition, conductive part of the myoelectric potential detecting portion 222 can be made not to be exposed. Therefore, the myoelectric artificial limb 221 of the present invention can be an artificial limb which is safe for the user and is water-resistant.

A rechargeable secondary battery can be used for the battery 111 provided in the myoelectric potential detecting portion 222. For example, an electric-double layer capacitor having a collector electrode, a polarizable electrode, a separator, or an electrolytic solution can be used. In the case of using the battery 111 provided in the myoelectric potential detecting portion 222 embedded in the body as in this embodiment mode, an electrolytic solution or an electrode which is safe for the human body is preferably selected.

Next, the artificial limb driving portion 223 is described in detail. The artificial limb driving portion 223 includes the driving portion 117 for operations, the drive control circuit 120 for driving and controlling the driving portion 117, a varied sensor 116 for detecting pressure, temperature, or the like, the central arithmetic processing circuit 115 which processes a driving control signal, a signal from the sensor, or the like, the transmitting/receiving circuit 113 for receiving a signal from the myoelectric potential detecting portion 222 and transmitting an electromagnetic wave or a magnetic flux for charging to the myoelectric potential detecting portion 222, the battery 119 for driving the artificial limb driving portion 223, and the charging circuit 118 for charging the battery 119.

In addition, the artificial limb driving portion 223 includes a cover which covers all the artificial limb driving portion 223. The artificial limb driving portion 223 is connected to an extremity stump portion by a socket using silicon and is fixed to the body of the user by a known method such as fixing the artificial limb driving portion 223 to an upper extremity or an lower extremity using a band. Note that the artificial limb driving portion 223 is preferably fixed so that it does not disturb operation of the artificial limb and other portions.

The driving portion 117 includes a driving mechanism having a skeleton and a joint, a wire, a sleeve, a motor for pressing and pulling the wire, an artificial muscle, and the like.

In order to realize complicated and flexible movement by the driving portion 117 and make the driving portion be used comfortably by the user of the artificial limb, it is preferable to use a mechanism which is similar to driving of an actual limb for the driving mechanism. For example, a tendon runs inside of a synovial sheath in a finger portion of an actual limb, and the tendon stops at a proximal phalanx, a middle phalanx, a distal phalanx, and a sheath of each finger depending on functions of the tendon. Then, the tendon moves when each muscle stretches, and each joint connected to the tendon moves.

In order to imitate this structure, a method can be used in which a cable which is fixed to each finger of the driving mechanism is inserted inside of a lubricated sleeve, and each joint of the driving mechanism is driven by pressing and pulling the cable by a motor or an artificial muscle, for example.

When a structure in which each joint of the driving mechanism is driven using a cable is employed as described above, the number of motors can be reduced and degree of freedom which is more than the number of motors can be realized because it is not necessary to provide a motor in each joint. Thus, power consumption and weight can be reduced.

In addition, an actuator which is formed using a high molecule can be used for the artificial muscle. By using the artificial muscle, power consumption and weight can be further reduced compared with the case of using the motor. Further, it is preferable to use a motor and an artificial limb having high durability and reliability.

The sensor 116 detecting pressure and temperature which are external stimuli may be provided on a surface of the artificial limb driving portion 223.

For example, a temperature sensor can detect temperature of an object which is touched by the artificial limb driving portion 223. In addition, a structure can also be used in which the user of the myoelectric artificial limb 221 can know temperature around the artificial limb driving portion 223 by a method of reproducing a sense on a skin surface such as an extremity stump portion using a heater, applying an appropriate stimulus to a sensory nerve, or the like.

In a risky condition for using the artificial limb such as high temperature, a structure can also be used in which the user of the artificial limb can know the risky condition by using warning indication using light or sound. Note that depending on applications of the artificial limb, a structure without a temperature sensor can be used.

When a pressure sensor is provided, pressure applied to the artificial limb device driving portion 223 can be detected. Generally, in the case where a human performs operations of grasping and picking using a hand, hardness and elasticity of an object to be grasped are predicted based on sight, experience, and the like, and pressure which should be applied to a finger is determined. Further, a muscle moves while always feeding back data on whether the hand touches an object or how much pressure is applied to the object by a tactile sense of the finger, i.e., pressure.

As one mode, the artificial limb driving portion 223 can have a structure in which data on a tactile sense is given to the user of the artificial limb by stimulating a sensory nerve based on data obtained by the pressure sensor. Alternatively, a structure can be employed in which excess and deficiency of grip force at the time of an operation such as grip are adjusted depending on operation patterns of the user of the artificial limb. In this case, the amount of adjustment is determined by the central arithmetic processing circuit 115 provided in the artificial limb driving portion 223. Note that the present invention is not limited to this mode, and the amount of adjustment may be determined by the central arithmetic processing circuit 108 provided in the myoelectric potential detecting portion 222 or the like.

For such a temperature sensor, a pressure sensor, or the like, a sensor which is formed using MEMS (micro electro mechanical system) technology can be used, for example. A sensor which is formed using MEMS technology is small, lightweight, and highly-sensitive. Therefore, weight of the artificial limb driving portion 223 can be reduced, a thin finger can be realized, and movement of the myoelectric artificial limb can be approximated to movement of real extremities.

The drive control circuit 120, the transmitting/receiving circuit 113, the charging circuit 118, and the battery 119 provided in the artificial limb driving portion 223 can be used similarly to Embodiment Mode 1.

As one mode, a receiving portion of the transmitting/receiving circuit 113 has a structure in which phase shift keying and decoding of a transmitted signal are performed using orthogonal frequency division multiplexing, and the signal is output to the central arithmetic processing circuit 115 as a digital signal having a plurality of channels. Alternatively, the receiving portion of the transmitting/receiving circuit 113 can have a structure in which demodulation and decoding of a transmitted signal are performed using a coiled antenna for channels which are necessary for communication using an electromagnetic induction method, and a digital signal having a plurality of channels is output to the central arithmetic processing circuit 115. Further alternatively, the receiving portion of the transmitting/receiving circuit 113 can have a structure in which demodulation and decoding of an optical signal are performed, and a digital signal having a plurality of channels is output to the central arithmetic processing circuit 115. Note that the myoelectric artificial limb of the present invention is not limited to such a mode, and can have a structure in which the artificial limb driving portion 223 and the myoelectric potential detecting portion 222 communicate with each other using various methods.

Data on a myoelectric potential which is transmitted from the myoelectric potential detecting portion 222 and is received by the transmitting/receiving circuit 113 provided in the artificial limb driving portion 223 is input to the central arithmetic processing circuit 115 of the artificial limb driving portion 223; the central arithmetic processing circuit 115 of the artificial limb driving portion 223 performs pattern recognition based on this data; and the central arithmetic processing circuit 115 of the artificial limb driving portion 223 determines a series of operations of a joint included in the artificial limb driving portion 223, such as flection, extension, pronation, supination, abduction, and adduction, which is necessary for the user.

Here, in the case of performing pattern recognition by the central arithmetic processing circuit 108 provided in the myoelectric potential detecting portion 222, for example, pattern recognition in the central arithmetic processing circuit 115 provided in the artificial limb driving portion 223 is not necessary.

When the necessary operations are determined by data processing as described above, in order to operate a motor or an artificial muscle corresponding to the operations, a signal is output to the drive control circuit 120.

In addition, data from the sensor 116 such as the temperature sensor, the pressure sensor, or the like provided in the artificial limb driving portion 223 is input to the central arithmetic processing circuit 115 of the artificial limb driving portion 223; the central arithmetic processing circuit 115 of the artificial limb driving portion 223 judges intention of the user of the artificial limb such as grasping or picking by a result of pattern recognition; and the central arithmetic processing circuit 115 of the artificial limb driving portion 223 adjusts power generated by the motor or the artificial muscle when needed.

Further, the arithmetic processing circuit 115 provided in the artificial limb driving portion 223 may have a learning function of pattern recognition. For example the arithmetic processing circuit 115 provided in the artificial limb driving portion 223 can have a function of learning based on the amount and an operation result of a myoelectric potential input to the myoelectric potential detecting portion 222, determining a parameter which is suitable for the user of the artificial limb to perform operations.

The charging circuit 118 provided in the artificial limb driving portion 223 includes a rectifier circuit which converts AC current input from an external power supply into DC current, a current-voltage control circuit for making rectified power into a suitable value for charging, a charging control circuit which controls power supplied to the battery 119, and the like. The power input from the external power supply is stored in the battery 119 through the charging circuit 118. The battery 119 which is charged as described above supplies power to each part of the artificial limb driving portion 223 in order to drive the whole artificial limb driving portion 223.

The battery 119 provided in the artificial limb driving portion 223 can also have a structure in which an electromagnetic wave which is transmitted from an external charger is received through the antenna 114 provided in the artificial limb driving portion 223, obtained AC current is output to the charging circuit 118 provided in the artificial limb driving portion 223 to change the battery 119 provided in the artificial limb driving portion 223. Specifically, a structure can be used in which change in magnetic flux generated from a coiled antenna included in the external charger is received by the coiled antenna provided in the artificial limb driving portion 223, and the received displacement current is output to the charging circuit 118 provided in the artificial limb driving portion 223.

The artificial driving portion 223 needs high power because it includes the driving portion 117 which includes the motor, the artificial muscle, or the like. However, it is preferable that the battery 119 provided in the artificial limb driving portion 223 be as lightweight as possible.

The myoelectric potential detecting portion 222 which is to be embedded in the body is preferably as small as possible in order to reduce a burden on the body to be embedded with the myoelectric potential detecting portion 222. One of elements which determine the size of the myoelectric potential detecting portion 222 can be the battery 111. Since the battery 111 can be made smaller as power consumption of the myoelectric potential detecting portion 222 is lower, a structure in which the number of signal processing performed by the central arithmetic processing circuit 108 provided in the myoelectric potential detecting portion 222 is reduced and necessary signal processing is performed by the central arithmetic processing circuit 115 provided in the artificial limb driving portion 223 can be used, for example. Alternatively, a method can be employed in which the battery 111 of the myoelectric potential detecting portion 222 is made smaller and charging is frequently performed at short time intervals.

In the case where the user takes off the artificial limb driving portion 223, the artificial limb preferably has a function of saving power by stopping the myoelectric potential detecting portion 222. In order to realize this function, a structure can be used in which an instruction to stop operations of the myoelectric potential detecting portion 222 or an instruction to stop operations of the myoelectric potential detecting portion 222 from the artificial limb detecting portion 223 can be given by determining whether the transmitting/receiving circuit 109 included in the myoelectric potential detecting portion 222 and the transmitting/receiving circuit 113 included in the artificial limb driving portion 223 are in the range of a distance where communication can be performed. When the myoelectric artificial limb 221 is water-resistant as described above, danger of an electric shock or electric leakage is removed, bathing, swimming, sports with sweating, and the like while putting on the myoelectric artificial limb 221 can be performed, and quality of life of the user can be improved.

Here, one mode and an operation method of the driving portion 117 are described with reference to FIG. 2, and FIGS. 11 to 14B.

As shown in FIG. 2, after a potential detected by the myoelectric potential electrode 104 of the myoelectric potential detecting portion 222 is amplified by the amplifier circuit 106 and the detected potential is converted into a digital signal by the A/D converter circuit 107, a series of operations of a joint included in the artificial limb driving portion 223 is determined by the central arithmetic processing circuit 108, and a digital signal corresponding to the operation is output. The transmitting/receiving circuit 109 modulates the digital signal and transmits the modulated digital signal to the antenna 114 provided in the artificial limb driving portion 223 through the antenna 112 provided in the myoelectric potential detecting portion 222 using an electromagnetic wave.

In the artificial limb driving portion 223, a signal transmitted from the myoelectric potential detecting portion 222 is received by the transmitting/receiving circuit 113 through the antenna 114. After that, data on a myoelectric potential which is transmitted from the myoelectric potential detecting portion 222 and is received by the transmitting/receiving circuit 113 is input to the central arithmetic processing circuit 115; pattern recognition is performed based on this data; and a series of operations of a joint included in the artificial limb driving portion 223, such as flection, extension, pronation, supination, abduction, and adduction, which is necessary for the user, is determined. The drive control circuit 120 generates current and voltage which are necessary for operations of the motor or the artificial limb of the driving portion 117 from the central arithmetic processing circuit 115 provided in the artificial limb driving portion 223.

The driving portion 117 includes a skeleton, a joint mechanism, and a driving mechanism. In addition, in order to protect the driving portion, the driving portion 117 may include a protective cover.

The skeleton corresponds to a human bone.

The joint mechanism corresponds to a human joint. Therefore, the joint mechanism is provided between skeletons (there is the case in which an end of a skeleton functions as the joint mechanism).

The driving mechanism corresponds to a human muscle. The driving mechanism uses a motor or an artificial muscle as a power source. The amount and the speed of movement of the motor or the artificial muscle are controlled by the drive control circuit 120. In this embodiment mode, the case in which the driving portion is driven mainly using a motor is described.

Silicon rubber may be used for the protective cover for beauty, dust prevention, water resistance, insulation, or the like. Alternatively, plastic can be used for lightweight, and these materials can be used properly depending on purposes.

Figure 11:
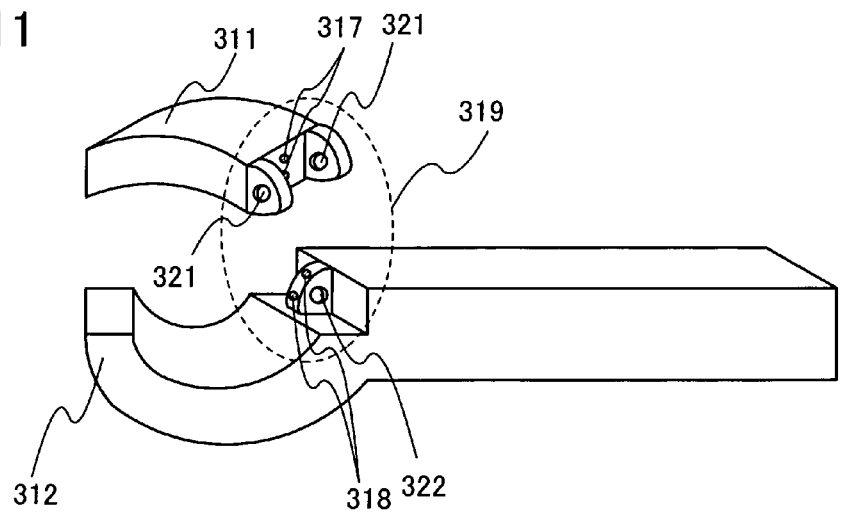
FIG. 11 illustrates a structure of an assist device of the present invention.
Figure 12A:
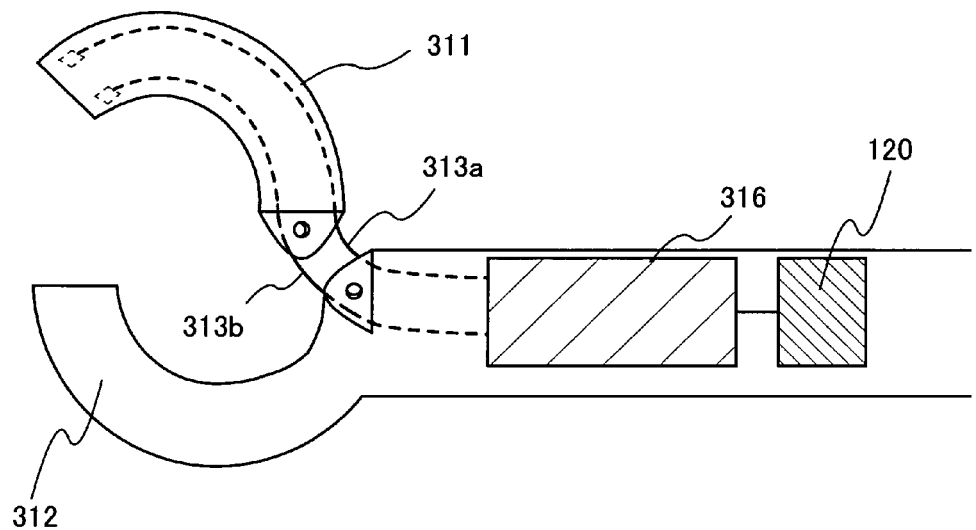
FIGS. 12A and 12B illustrate structures of an assist device of the present invention.
Figure 12B:
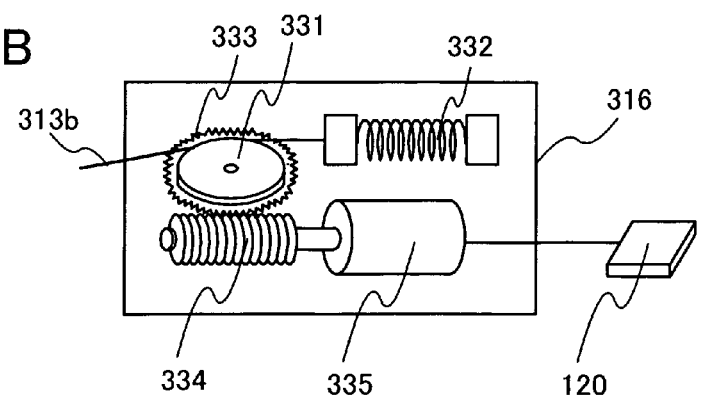
Figure 13:
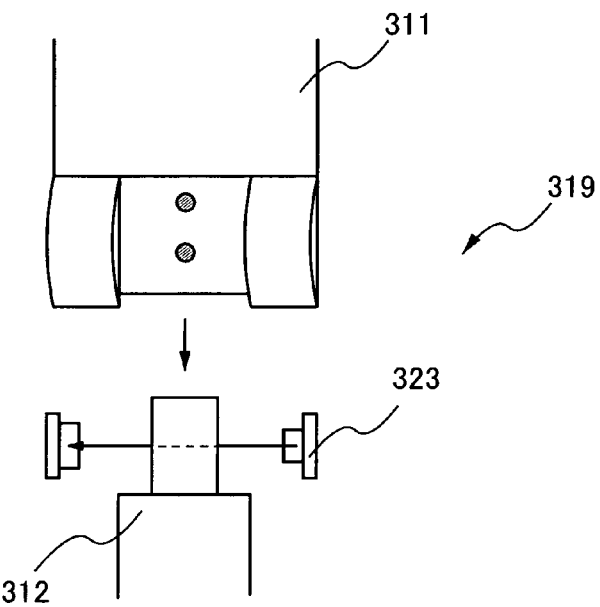
FIG. 13 illustrates a structure of an assist device of the present invention.

First, structures of the driving portion 117 are described with reference to FIGS. 11 to 14 using simple models. Here, the driving portion 117 is a model having an opening and closing mechanism for sandwiching an object. FIG. 11 is a perspective view of the driving portion 117. FIGS. 12A and 12B are top views of the driving portion 117. FIG. 13 is a diagram of the joint mechanism.

As shown in FIGS. 11 to 12B, the driving portion 117 includes a movable skeleton 311, a fixed skeleton 312, wires 313a and 313b, and a driving portion 316. The movable skeleton 311 and the fixed skeleton 312 include a joint mechanism 319 so that ends of respective skeletons are combined with each other and can move (therefore, in this case, part of the skeletons forms the joint mechanism). In addition, the driving portion drives the fixed skeleton 312 by the driving mechanism and the joint mechanism so that the movable skeleton 311 opens and closes.

As shown in FIGS. 11 and 13, the joint mechanism 319 is provided so that the movable skeleton 311 and the fixed skeleton 312 are combined like a hinge. Therefore, movable skeleton-side joint holes 321 and a fixed skeleton-side joint hole 322 are provided at the end of the movable skeleton and the end of the fixed skeleton, respectively, and the joint mechanism includes a pin 323 which is to pass through these joint holes. When the joint mechanism is formed with such a structure, an uniaxial operation (an opening and closing operation) can be realized.

In addition, as shown in FIG. 12A, the movable skeleton 311 includes wire fixing tools 314, and the movable skeleton 311 and the fixed skeleton 312 include wire drawing-in pipes 317 and 318 for passing the wire inside. However, the wire can be provided not inside the skeletons but outside the skeletons and driving can be performed. In that case, wire drawing-in pipes are not necessary. Further, in that case, wire fixing tools may also be provided outside the skeletons. In this embodiment mode, an example in which a wire is provided inside the skeletons is shown.

The wire fixing tools 314 are provided inside at the time of performing a sandwiching operation by the movable skeleton 311 and outside which is an opposite surface (when likening to a muscle included in the human body, the wire fixing tools 314 are provided at stop positions of a flexor and an extensor for performing an opening and closing operation (=a flexing and extending operation)).

In this example, the driving portion 316 includes two wires 313a and 313b and the wires 313a and 313b are connected to the above-described two wire fixing tools 314. In addition, the movable skeleton 311 and the fixed skeleton 312 include the wire drawing-in pipes 317 and 318 for passing the two wires 313a and 313b. The wires 313a and 313b fixed to the wire fixing tools 314 of the movable skeleton 311 pass inside the fixed skeleton 312 through the joint mechanism and are connected to the driving portion 316.

As shown in FIG. 12B, the driving portion 316 includes a pulley 331, a spring 332, a gear 333, a worm gear 334, a motor 335, and the like. Here, although a position where the driving mechanism is provided is not limited, an example in which the driving portion 316 is provided in the fixed skeleton 312 is shown in this embodiment mode. When the driving mechanism is stored in the skeleton as described above, the driving portion 316 can be made smaller.

The wires 313a and 313b which pass through the movable skeleton 311 and the fixed skeleton 312 are wound around the pulley 331. Ends of the wires 313a and 313b are connected to the spring 332. The spring 332 is fixed inside the fixed skeleton 312 (when likening to a muscle included in the human body, the spring 332 is fixed to an origin of a flexor and an extensor)

Although FIG. 12 B shows a view in which the wire 313b is wound around the pulley 331, the wire 313a is wound around another pulley 331 similarly.

The spring 332 prevents the wires 313a and 313b from slack and being pulled firmly of by tension of the spring 332. Therefore, in the case where a driving portion which performs simple operations is acceptable, a spring is not necessary and an end of a wire which is wound around the pulley may be directly fixed to the fixed bone 312. However, when a wire is fixed through a spring, a margin can be given to an operation of flection or extension, so that more favorable movement can be realized.

The pulley 331 is fixed to the gear 333 and the gear 333 engages with worm gear 334. The worm gear 334 is fixed to the motor 335. Thus, rotation of the motor 335 is transmitted to rotation of the pulley 331, and the wires 313a and 313b can be pulled and loosened.

Figure 14A:
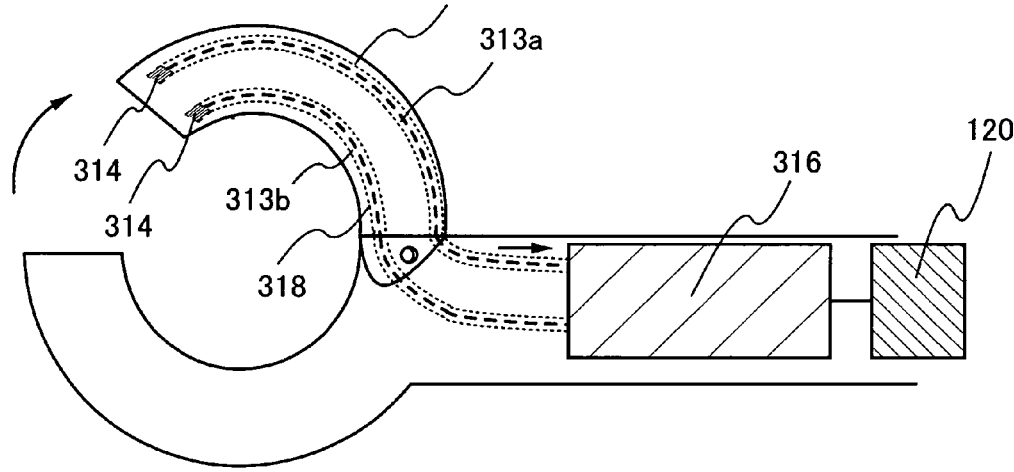
FIGS. 14A and 14B illustrate a structure of an assist device of the present invention.
Figure 14B:
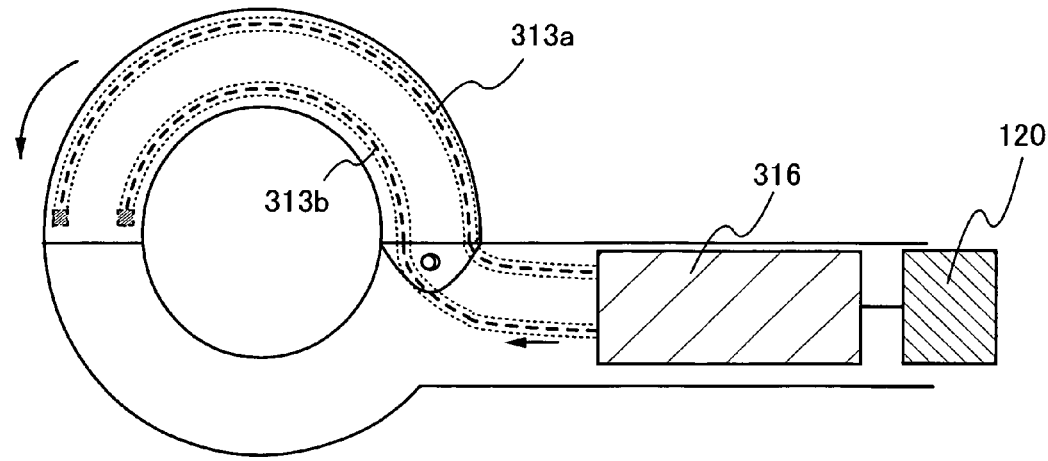

When the two wires are separately pulled by the driving mechanism having the above-described structure, the movable skeleton 311 can be moved. For example, as shown in FIGS. 14A and 14B, when the wire 313b fixed to the inside wire fixing tool is pulled, the movable skeleton 311 moves so as to be in contact with the fixed skeleton 312 side, i.e., performs a picking operation. In addition, when the wire 313a fixed to the outside wire fixing tool is pulled, the movable skeleton 311 moves so as to be separate from the fixed skeleton 312, i.e., performing an opening operation.

At this time, it is necessary to loosen a wire which is not related to the operation, i.e., a wire which is not pulled. For example, in the case of performing a sandwiching operation by pulling the wire 313b fixed to the inside wire fixing tool, it is necessary to loosen the wire 313a fixed to the outside wire fixing tool so that it does not impede sandwiching. Therefore, in this embodiment mode, it is necessary to control pulling and loosening of the two wires even in the case of performing one operation.

Here, when a structure is used in which the driving portion 316 is fixed sideways as shown in the drawings, the movable skeleton 311 opens in a direction which is opposite to gravity, and the movable electrode 316 closes without application of force for opening, only a wire for opening (the wire fixed to the outside wire fixing tool) can be provided.

This can be realized by using a structure in which the two skeletons always perform a sandwiching operation (a closing operation) using the joint mechanism and the movable skeleton is opened or not opened (i.e., closed), without limiting to a structure in which gravity is used.

In the case of performing a uniaxial operation as described above, driving may be performed using two wires; however, by fixing one of operations as described above and having a structure of an operation such as performing or not performing an opposite operation, the wires and the driving mechanism can be collected. Therefore, the number of components of the driving portion can be reduced, so that the driving portion can be reduced in size and weight.

Next, the case in which the assist device of the present invention is used as a human artificial limb is described. In the model of the driving portion, a simple uniaxial operation such as opening and closing is performed. However, a human's hand performs complicated and delicate operations such as holding, picking, pressing a button, and the like. Thus, the case in which the assist device 101 of the present invention is used as a driving portion of an artificial limb having a skeleton which is close to a human bone, i.e., an artificial limb which can reproduce movement of the limb is described below.

In addition, since the skeleton is close to the human bone in this example, in order to easily understand a provision relation of each part forming the skeleton, each part forming the skeleton is referred to as "~~skeleton". Note that a name of each part forming the skeleton "~~skeleton" corresponds to a name of the human bone "~~bone".

The driving portion 117 includes a skeleton, a joint mechanism, a driving mechanism, a wire, and the like, similarly to the above-described example.

First, a skeleton of the assist device (the artificial limb) forming an upper extremity is described. An actual limb includes 19 movable bones, and thus complicated operations of the limb can be realized. It is preferable that a hand portion of the driving portion 117 include 19 movable skeletons similarly to an actual bone also in this example.

Figure 15:
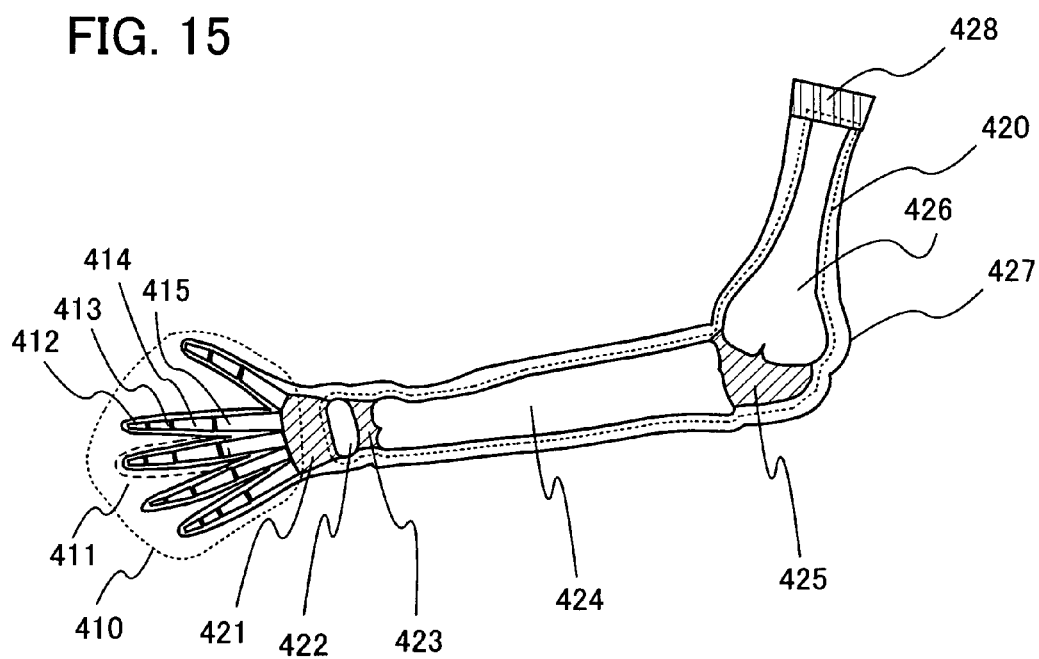
FIG. 15 illustrates a structure of an assist device of the present invention.

Therefore, as shown in FIG. 15, the skeleton includes a skeleton of a hand 410 forming five fingers (the skeleton of the hand 410 includes distal skeletons 412, middle skeletons 413, finger skeletons 411 formed from proximal skeletons 414, and metacarpal skeletons 415. Note that a finger skeleton of a first finger is formed of the distal skeleton and the proximal skeleton), and an artificial hand proximal skeleton 420 which is connected the skeleton of the hand 410 through the joint mechanism. In addition, the finger skeletons 411 and the artificial hand proximal skeleton 420 may be covered with a cover 427. Further, a socket 428 which connects the artificial limb driving portion 223 and the human body is provided.

These skeletons are preferably formed using materials which are lightweight and have high durability such as plastic and titanium in order to lighten the assist device and realize nimble operability. However, the present invention is not limited to these materials.

For example, in the case where the skeleton of the hand 410 provides a particular function for a particular operation or in the case where the bone of the hand 410 does not need complicated functions like an actual hand, the finger skeletons 411 corresponding to a plurality of fingers may be collected into one wide skeleton. For example, a structure can be used in which finger skeleton of second to fifth fingers and the metacarpal skeleton are collected and the first finger is independent like a mitten.

As shown in FIG. 15, each of the proximal skeletons 414 and the metacarpal skeletons 415 has a columnar shape having the length and a diameter based on each of finger skeletons and metacarpal skeletons. Since an actual finger becomes thinner as an end, each of these skeletons preferably has a columnar shape which becomes thinner as an end.

Opposite ends of each of the finger skeletons and the metacarpal skeletons has the hinge structure described in the above-described example to form a joint mechanism using adjacent skeletons. Note that a joint mechanism is not provided at ends of the distal skeletons (in the diagram, the joint mechanism of the finger skeleton and the like are omitted). When the joint mechanism of the hinge structure is provided between each of the finger skeletons and the metacarpal skeletons as described above, operations corresponding to flection and extension of a finger can be performed.

In addition, each of the distal skeletons 412 may have a shape in which thickness becomes thinner toward the end. Thus, a gap for providing a sensor is formed at an end (i.e., a finger tip) of the driving portion 117 and an actual finger has such a structure, which is good for appearance.

Further, since the metacarpal skeletons 415 are located inside of a palm of the artificial hand, the length thereof is not necessarily based on the length of metacarpal bones. Therefore, the length of the metacarpal skeletons is shorter than the length of metacarpal bones, and in a gap therebetween, a joint mechanism between each of the finger skeletons 411 and the carpal skeleton 422, and a driving mechanism for driving each of the finger skeletons 411 can be provided. Here, the first finger and the second to fifth fingers have different movable directions and the like.

Therefore, the joint mechanism between each of the finger skeletons 411 and the carpal skeleton 422 includes a first joint mechanism provided between a middle finger skeleton of the first finger and the carpal skeleton and a second joint mechanism provided between middle finger skeletons of the second to fifth fingers and the carpal skeleton.

Since the first finger performs a rotation operation unlike other fingers, the first finger includes a driving mechanism which drives the first finger through the first joint mechanism.

A driving mechanism which performs an operation of opening a hand (specifically, an operation of opening the second finger to the first finger side and opening the fourth and fifth finger to the outside of the fifth finger) can be provided. For example, this driving mechanism can be formed using a fixed axis of the finger skeleton, a spring for suppressing natural opening of the finger skeleton, a gear engaging with a gear fixed to the metacarpal skeleton, a motor fixed to the gear, and the like. Alternatively, a structure can be used in which such a shape of the hand is formed by a shape of the skeleton of the hand and such a driving mechanism is not provided.

Next, the artificial hand proximal skeleton 420 is described. In the case of using the assist device as an artificial hand, the artificial hand proximal skeleton 420 includes a carpal skeleton 422 which is connected to a joint mechanism 421, a forearm skeleton 424 which is connected to the carpal skeleton 422 through a joint mechanism 423, and a brachio skeleton 426 which is connected to the forearm skeleton 424 through a joint mechanism 425.

Although actual metacarpal bones have eight or nine bones, movement of the hand can be almost realized by using the finger skeletons and the metacarpal skeletons. Therefore, the carpal skeleton 422 can be formed using one skeleton. Needless to say, the present invention is not limited to this, and the carpal skeleton 422 may be formed using two or more skeletons.

In addition, although an actual forearm bone can perform a pronation operation, a supination operation, and the like by including two bones of a radius and an ulna, the forearm skeleton 424 can be formed using one skeleton because the driving portion 117 can compensate a pronation operation, a supination operation, and the like by the joint mechanism or the driving mechanism.

In addition, although the structure in which the driving portion 117 includes skeletons up to the brachio skeleton 426 in this example, needless to say, a brachio skeleton is not necessary when the user of the artificial limb only needs skeletons beyond a forearm.

Next, the joint mechanism of the driving portion 117 is described. As a joint, there are a uniaxial hinge joint, a biaxial saddle joint, a triaxial carpal joint, and the like depending on functions. Since all the joints of second to fifth fingers and a finger joint of a first finger are uniaxial movements of extension in an actual hand, a joint mechanism of a hinge structure is provided between skeletons thereof.

However, a joint of a root of the first finger (a joint between a metacarpal bone and a carpal bone of the first finger) includes a biaxial saddle joint in which orthogonal movement is added to movement of a hinge joint, unlike other fingers. Therefore, a joint mechanism between the metacarpal skeleton and the carpal skeleton of the first finger realizes movement which is similar to that of the actual first finger by including a hinge joint at upper part as a joint according to the biaxial saddle joint and a hinge joint which is orthogonal to it at lower part, or including a joint mechanism of a rotational structure. An joint structure having such multi-axial movement is similar to the joint mechanism 423 between the carpal skeleton 422 and the forearm skeleton 424 and the joint mechanism 425 between the forearm skeleton 424 and the brachio skeleton 426.

Each of the skeletons realizes movement of a joint by pulling (or loosening) a wire passing through the inside. Running and a power source of the wire are described below.

As shown in the movable skeleton 311 shown in FIG. 12A, the distal skeletons 412 includes two wire drawing-in pipes for passing wires inside and wire fixing tools for fixing the wires around the center of the inside of the distal skeletons 412. As shown in the movable skeleton 311 shown in FIG. 12A, the wire fixing tools are provided on the palm side and the back of the hand side, respectively (when likening to a muscle included in the human body, the wire fixing tools are provided at stop positions of a flexor and an extensor).

The middle skeletons 413 also include two wire drawing-in pipes and wire fixing tools. However, since extension of the middle skeletons 413 can be substituted for extension of the distal skeletons 412, the middle skeletons 413 can have a structure in which wire fixing tools are included only at a position corresponding to a muscle stop portion on the flexor side.

In order to realize complicated movement of each finger, each of the proximal skeletons 414 and the metacarpal skeletons 415 include three wire drawing-in pipes and wire fixing tools. The plurality of wires fixed to each of the skeletons as described above are connected to the driving mechanism through each of the finger skeletons and the wire drawing-in pipes provided in the metacarpal skeletons 415.

Similarly to the movable skeleton 311 shown in FIG. 12A, each of the wires connected to the driving mechanism is rolled up by the pulley, the end thereof is connected to the spring, and the spring is fixed to inside or around the metacarpal skeletons 415 or the carpal skeleton 422 (when likening to the human body, the spring is fixed to an origin of each muscle or around the origin of each muscle). In addition, similarly to the movable skeleton 311 shown in FIG. 12A, a structure without the spring may be used. The pulley is fixed to the gear and the gear engages with the worm gear. The worm gear is fixed to the motor through a shaft. Thus, rotation of the motor is transmitted to rotation of the pulley and the wires can be pulled and loosened.

When the wire fixed to the wire fixing tool located at an extensor stop portion is pulled, each finger is bent. Then, when the wire fixed to the wire fixing tool located at the extensor stop portion is pulled, each finger is extended. This fixing structure of the wire is similar to the case of driving the artificial hand proximal skeleton.

The metacarpal skeleton of the first finger needs to rotate in order to perform an operation of picking an object, or the like. In the case where a joint mechanism of a rotational structure between the metacarpal skeleton of the first finger and the carpal skeleton 422, the driving mechanism which drives the joint mechanism has a rotational axis and a pin of the rotational axis engages with a groove provided in a motor bearing. Thus, the driving mechanism is fixed. When the driving mechanism has such a structure, an operation which is closer to a rotational operation of the human body can be realized. The same can be said for other skeletons having multi-joints.

When the joint mechanism provided between respective skeletons and the driving mechanism which drives respective skeletons are combined intricately as described above, the assist device having a function as an artificial hand can be driven.

Here, the gear and the worm gear preferably has a structure with a little backlash as much as possible (here, a backlash corresponds to a gap between a screw and a gear at the time of dealing a machine. Since this gap is provided, the screw and the gear can freely move. However, when the machine rotates in a certain direction to a reverse direction, there is a possibility that misalignment in size is caused due to the backlash). In order to reduce the backlash, a cog of the gear may be a rotational roller. In addition, the motor preferably has high positional accuracy, and for example, a stepping motor may be used.

In this example, the driving portion 117 which is driven by passing a wire inside of the skeleton and pulling or loosening it is shown. However, the assist device 101 of the present invention is not limited to this example. For example, the wire for driving each of the skeletons can be provided on the surface of each of the skeletons. In addition, an artificial muscle can be used for driving each of the skeletons. An artificial muscle contracts by a stimulus such as an electric stimulus or pressure and behaves similarly to a human's muscle. For example, an artificial muscle is formed using a conductive high molecule or the like which contracts by voltage application. In the above-described example, the driving mechanism and the wire can be replaced with this artificial muscle. It is acceptable as long as the artificial muscle is fixed to the origin of the muscle, around the origin of the muscle, or a stop portion of the muscle, similarly to the human's muscle.

In addition, the drive control circuit 120 controls movement of the driving mechanism or the artificial limb by receiving a signal output from the central arithmetic processing circuit 115 provided in the artificial limb driving portion 223 shown in FIG. 2. Specifically, the drive control circuit 120 generates current and voltage which are necessary for driving the motor included in the driving mechanism shown in FIG. 15 or the artificial muscle.

Next, skeletons of the assist device (the artificial limb) forming a lower extremity are described.

Although the first to fifth fingers are described in the upper limb, first to fifth toes are described in the lower limb. The first to fifth toes include finger skeletons and metatarsal skeletons similarly to the skeletons which form the first to fifth fingers, and the metatarsal skeletons are connected to tarsal skeletons through the joint mechanism. The tarsal skeletons are connected to crural skeletons through the joint mechanism, and the crural skeletons are connected to femoral skeletons through the joint mechanism.

Although an actual crural skeleton includes two bones of a tibial bone and a fibula, a crural skeleton which forms the driving portion can be formed using one skeleton. Further, although a structure in which the driving portion includes up to the femoral skeleton is shown in this example, needless to say, a femoral skeleton is not necessary when the user of the artificial limb only needs skeletons beyond a crural skeleton.

Further, although the lower limb includes similar bones to the upper limb, the lower limb does not perform complicated movement compared to the upper limb. Therefore, the structure of the lower limb can be simplified by collecting the bones which form the crus. For example, the tarsal skeletons can be formed using one bone (similarly to the carpal skeleton). Similarly, the metatarsal skeletons may be formed using one skeleton.

However, there are a plurality of joints between metatarsal bones and tarsal bones and it is considered that the plurality of joints have important functions for maintaining balance at the time of standing or walking. Thus, in the case of forming the assist device as an artificial limb of the lower limb, a structure may be used in which the metatarsal skeletons and the tarsal skeletons are formed using a plurality of skeletons and movement of actual bones can be recreated.

The lower limb can be driven by the wires, the driving mechanism which pulls and loosens the wires, and the joint mechanism provided between the respective skeletons, similarly to the upper limb. One end of a wire which substitutes main movement of a muscle is fixed to a stop portion of the muscle, and the other end thereof is fixed to the origin of the muscle through the driving mechanism. In addition, the joint mechanism provided between the respective skeletons includes uniaxial to triaxial joint mechanism in accordance with each of the joints.

Thus, the myoelectric artificial limb 221 functioning as the upper extremity or the lower extremity can be provided.

When a wireless charging means (an RF battery) is employed for the myoelectric potential detecting portion 222 as described in this embodiment mode, power charged in the battery of the artificial limb driving portion 223 can be supplied to the myoelectric potential detecting portion 222 wirelessly. Therefore, the artificial limb driving portion 223 which has a high voltage portion and the myoelectric potential detecting portion 222 which is in contact with a human body are electrically separated, so that the myoelectric artificial limb 221 which has high security can be provided. Further, in the present invention, since connection without using a terminal can be performed by unwiring communication between the myoelectric potential detecting portion 222 and the artificial limb driving portion 223, the myoelectric artificial limb 221 which can be easily changed in accordance with growth stages or applications can be provided.

Embodiment Mode 3

Figure 5:
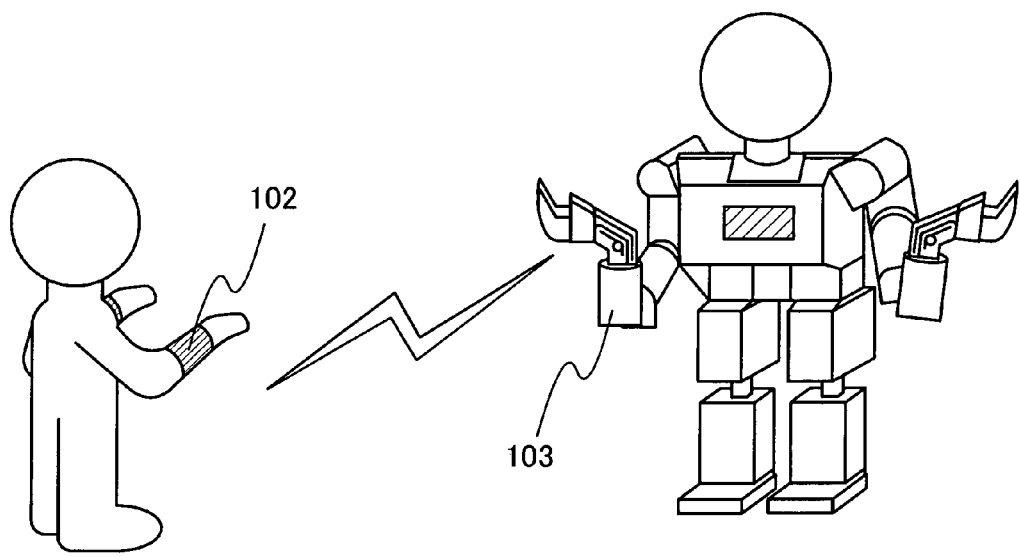
FIG. 5 illustrates an application of an assist device of the present invention.

In this embodiment mode, an application mode of an assist device, which is different from that of Embodiment Mode 2, is described. In this embodiment mode, a mode in which remote control of the assist device driving portion can be performed even when a distance between a detecting portion and the assist device driving portion is far is described with reference to FIGS. 1 and 5.

The detecting portion 102 is provided in extremities of the user. In addition, the assist device driving portion 103 is provided in extremities of a driving device (a robot) in which remote control can be performed. The first sensor of the detecting portion 102 detects movement of the extremities as a biosignal. Next, the biosignal is processed by the amplifier circuit 106, the A/D converter circuit 107, and the central arithmetic processing circuit 108 provided in the detecting portion. The processed signal is transmitted from the transmitting/receiving circuit 109 to the assist device driving portion 103 through the antenna 112.

In the assist device driving portion 103, the signal transmitted from the detecting portion 102 is received by the transmitting/receiving circuit 113 through the antenna 114. The signal received by the transmitting/receiving circuit 113 is processed by the central arithmetic processing circuit 115 and the drive control circuit 120 similarly to Embodiment Mode 1, so that the driving portion 117 can be driven.

In addition, power which is obtained from an external power supply or a battery by the assist device driving portion 103 can be supplied to the detecting portion 102. Specifically, the power which is obtained from the external power supply or the battery by the assist device driving portion 103 is transmitted to the detecting portion 102 through the transmitting/receiving circuit 113 and the antenna 114 of the assist device driving portion 103.

In the detecting portion 102, the signal transmitted from the assist device driving portion 103 is received by the transmitting/receiving circuit 109 through the antenna 112. The signal received by the transmitting/receiving circuit 109 is processed by the charging circuit 110 similarly to Embodiment Mode 1, so that the battery 111 can be charged.

Further, power charged in the battery is supplied in order to operate the circuits provided in the detecting portion 102. Therefore, the detecting portion 102 does not need a cord from the external power, a cord which is necessary for exchanging signals with the assist device or conveying electromagnetic waves, or the like, so that the detecting portion 102 can be cordless. Accordingly, the detecting portion 102 can be easily used.

Moreover, when accuracy of detection of the first sensor 100 included in the detecting portion 102 is increased, data obtained from the first sensor 100 is precisely processed, and a second sensor which has high sensitivity and is selected from various kinds of sensors is provided, movement of the assist device driving portion 103 can be controlled with high accuracy. Even when a distance between the detecting portion 102 and the assist device driving portion 103 is far, remote control of the assist device driving portion 103 can be performed using a communication repeater.

As described above, when the assist device driving portion 103 of the assist device 101 of the present invention is provided in part of or all the extremities of a robot and in the body of the user of the detecting portion 102, remote control of the assist device driving portion 103 can be performed. In addition, in order to perform operations in particular circumstances such as outer space and deep ocean, risky operations, or the like, the assist device driving portion 103 can be used as a robot (see FIG. 5).

Note that this embodiment mode can be freely combined with any of the above-described embodiment modes.

Embodiment Mode 4

In this embodiment mode, an example of a method for manufacturing the detecting portion of the assist device shown in Embodiment Modes 1 to 3 is described with reference to the drawings. Although the detecting portion of the assist device can be formed by using a field effect transistor using a semiconductor substrate or an SOI substrate, a structure in which an antenna, a charging circuit, and a transmitting/receiving circuit are provided over the same substrate is described in this embodiment mode. Note that when an antenna, a charging circuit, a transmitting/receiving circuit, a central arithmetic processing circuit, an amplifier circuit, and the like are formed over a substrate at one time, and thin film transistors are used as transistors included in the charging circuit and the transmitting/receiving circuit, downsizing can be realized, which is preferable.

First, as shown in FIG. 6A, a separation layer 1903 is formed over one surface of a substrate 1901 with an insulating film 1902 interposed therebetween. Sequentially, an insulating film 1904 functioning as a base film and a semiconductor film 1905 (e.g., a film including amorphous silicon) are stacked. Note that the insulating film 1902, the separation layer 1903, the insulating film 1904, and the semiconductor film 1905 can be sequentially formed.

The substrate 1901 is selected from a glass substrate, a quartz substrate, a metal substrate (e.g., a stainless steel substrate), a ceramic substrate, a semiconductor substrate such as a silicon substrate, or the like. In addition, a substrate formed using polyethylene terephthalate (PET), polyethylene naphthalate (PEN), polyether sulfone (PES), acryl, or the like can be selected as a plastic substrate. Note that in this step, the separation layer 1903 is provided over the entire surface of the substrate 1901 with the insulating film 1902 interposed therebetween; however, when needed, the separation layer 1903 may be selectively provided by photolithography after the separation layer is formed over the entire surface of the substrate 1901.

The insulating film 1902 and the insulating film 1904 are formed by using an insulating material such as silicon oxide, silicon nitride, silicon oxynitride, or silicon nitride oxide by CVD, sputtering, or the like. For example, in the case where each of the insulating films 1902 and 1904 is formed with a two-layer structure, a silicon nitride oxide film may be formed as a first layer, and a silicon oxynitride film may be formed as a second layer. Alternatively, a silicon nitride film may be formed as the first layer and a silicon oxide film may be formed as the second layer. The insulating film 1902 functions as a blocking layer which prevents an impurity element from being mixed into the separation layer 1903 or an element formed thereover from the substrate 1901. The insulating film 1904 functions as a blocking layer which prevents an impurity element from being mixed into an element formed over the separation layer 1903 from the substrate 1901 and the separation layer 1903. By forming the insulating films 1902 and 1904 which function as the blocking layers, the case can be prevented in which alkaline metal such as Na or alkaline earth metal from the substrate 1901 and an impurity element included in the separation layer adversely affect the element formed over the separation layer 1903. Note that in the case where quartz is used for the substrate 1901, the insulating films 1902 and 1904 may be omitted.

A metal film, a stacked-structure of a metal film and a metal oxide film, or the like can be used for the separation layer 1903. The metal film is formed with a single-layer structure or a stacked-layer structure of a film of an element selected from tungsten (W), molybdenum (Mo), titanium (Ti), tantalum (Ta), niobium (Nb), nickel (Ni), cobalt (Co), zirconium (Zr), zinc (Zn), ruthenium (Ru), rhodium (Rh), palladium (Pd), osmium (Os), iridium (Ir), or silicon (Si), or an alloy material or a compound material which includes any of these elements as a main component. In addition, these materials can be formed by using various kinds formation methods of a thin film, such as sputtering and CVD. In order to obtain the stacked-structure of the metal film and the metal oxide film, plasma treatment in oxygen atmosphere or dinitrogen oxide atmosphere is performed or heat treatment in oxygen atmosphere or dinitrogen oxide atmosphere is performed after the above-described metal film is formed, so that oxide or oxynitride of the metal film can be provided on a surface of the metal film. For example, in the case of providing a tungsten film by sputtering, CVD, or the like as the metal film, plasma treatment is performed on the tungsten film so that a metal oxide film which is formed using tungsten oxide can be provided on a surface of the tungsten film. In this case, tungsten oxide is denoted by $WO_x$, where x is 2 to 3. There are cases where x is 2 ($WO_2$), x is 2.5 ($W_2O_5$), x is 2.75 ($W_4O_{11}$), x is 3 ($WO_3$), and the like. In forming tungsten oxide, a value of x is not limited to the above-described examples, and which kind of oxide is to be formed may be determined based on the etching rate or the like. In addition, for example, after forming a metal film (e.g., tungsten), metal oxide may be formed over the metal film (e.g., tungsten oxide may be formed over tungsten) at the same time as an insulating film of silicon oxide ($SiO_2$) or the like is formed over the metal film by sputtering. Further, high-density plasma treatment may be performed as plasma treatment. Metal nitride or metal oxynitride may be used in addition to the metal oxide film. In this case, plasma treatment or heat treatment may be performed on the metal film in nitrogen atmosphere or nitrogen and oxygen atmosphere.

The semiconductor film 1905 is formed with a thickness of 10 to 200 nm (preferably, 30 to 150 nm) by sputtering, LPCVD, plasma CVD, or the like.

Next, the semiconductor film 1905 is irradiated with laser light to be crystallized. Note that the semiconductor film 1905 may be crystallized by a method in which laser light irradiation is combined with thermal crystallization using RTA or an annealing furnace or thermal crystallization using a metal element which promotes crystallization. After that, an obtained crystalline semiconductor film is etched into a desired shape to form crystalline semiconductor films 1905a to 1905f as shown in FIG. 6B, and a gate insulating film 1906 is formed so as to cover the crystalline semiconductor films 1905a to 1905f.

The gate insulating film 1906 is formed by using an insulating material such as silicon oxide, silicon nitride, silicon oxynitride, or silicon nitride oxide by CVD, sputtering, or the like. For example, in the case where the gate insulating film 1906 is formed with a two-layer structure, a silicon nitride oxide film may be formed as a first layer, and a silicon oxynitride film may be formed as a second layer. Alternatively, a silicon nitride film may be formed as the first layer and a silicon oxide film may be formed as the second layer.

An example of manufacturing steps of the crystalline semiconductor films 1905a to 1905f is briefly described below. After a semiconductor layer having an amorphous structure is formed by a known method (e.g., sputtering, LPCVD, or plasma CVD), a resist mask is formed by using a crystalline semiconductor layer which is obtained by performing a known method of crystallization (e.g., laser crystallization, thermal crystallization, or thermal crystallization using a catalyst such as nickel) as a photomask, and then, the crystalline semiconductor layer is etched into a desired shape to form the crystalline semiconductor films 1905a and 1905f.

As a laser oscillator which is used for crystallization, a continuous wave laser beam (a CW laser beam) or a pulsed laser beam can be used. As a laser beam which can be used here, laser beams which are emitted from one or a plurality of laser beams from a gas laser such as an Ar laser, a Kr laser, or an excimer laser, a laser using a medium in which one or a plurality of elements of Nd, Yb, Cr, Ti, Ho, Er, Tm, and Ta is added as a dopant into single crystals of YAG; $YVO_4$, forsterite ($Mg_2SiO_4$), $YAlO_3$, or $GdVO_4$, or polycrystals (ceramic) of YAG, $Y_2O_3$, $YVO_4$, $YAlO_3$, or $GdVO_4$, a glass laser, a ruby laser, an alexandrite laser, a Ti:sapphire laser, a copper vapor laser, or a gold vapor laser can be given. By laser beam irradiation with a fundamental wave of such laser beam and a second harmonic wave to a fourth harmonic wave of the fundamental wave of such laser beam, a crystal having a large particle size can be obtained. For example, a second harmonic wave (532 nm) or a third harmonic wave (355 nm) of an Nd:$YVO_4$ laser (having a fundamental wave of 1064 nm) can be used. At this time, power density of the laser is required to be about 0.01 to 100 $MW/cm^2$ (preferably, 0.1 to 10 $MW/cm^2$). Irradiation is performed by setting the scan speed at about 10 to 2000 cm/sec. Note that the using a medium in which one or a plurality of elements of Nd, Yb, Cr, Ti, Ho, Er, Tm, and Ta is added as a dopant into single crystals of YAG, $YVO_4$, forsterite ($Mg_2SiO_4$), $YAlO_3$, or $GdVO_4$, or polycrystals (ceramic) of YAG, $Y_2O_3$, $YVO_4$, $YAlO_3$, or $GdVO_4$, an Ar ion laser, or the Ti:sapphire laser can be continuously oscillated, and can also be pulsed oscillated with a repetition rate of 10 MHz or more by performing a Q-switch operation, mode locking, or the like. When the laser beam is emitted with the repetition rate of 10 MHz or more, a semiconductor film is irradiated with the next pulse during the period in which the semiconductor film is melted by the laser beam and solidified. Accordingly, a solid-fluid interface can be continuously moved in the semiconductor film so that crystal grains which have grown continuously in the scan direction can be obtained, unlike the case of using a pulsed laser with a low repetition rate.

As crystallization treatment of the semiconductor layer having an amorphous structure, an SLS (sequential lateral solidification) method may be used. An SLS method is a method in which a sample is irradiated with pulsed excimer laser light through a slit mask. Specifically, an SLS method is a method in which, by performing crystallization by shifting a relative position of a sample and laser light by about the length of a crystal obtained by super lateral growth every one shot, crystals by super lateral growth controlled artificially are sequentially formed.

In addition, the gate insulating film 1906 may be formed by performing the above-described high-density plasma treatment on the semiconductor films 1905a to 1905f and oxidizing or nitriding surfaces thereof. For example, the gate insulating film 1906 is formed by plasma treatment with a mixed gas of noble gas such as He, Ar, Kr, or Xe, and oxygen, nitrogen dioxide, ammonia, nitrogen, or hydrogen. When excitation of plasma in this case is performed with introduction of a microwave, plasma with a low electron temperature and high density can be generated. By oxygen radical (there is the case in which OH radical is included) or nitrogen radical (there is the case in which NH radical is included), the surface of the semiconductor films can be oxidized or nitrided.

By such treatment using high-density plasma, an insulating film of 1 to 20 nm, typically, 5 to 10 nm is formed over the semiconductor film. Since reaction in this case is solid-phase reaction, interface state density between the insulating film and the semiconductor films can be extremely lowered. Since such plasma treatment directly oxidizes (or nitrides) the semiconductor films (crystalline silicon or polycrystalline silicon), variation in the thickness of the insulating film which is formed can be extremely reduced, ideally. In addition, since oxidization is not strongly performed in the crystal grain boundary of crystalline silicon, an extremely preferable state is obtained. That is, by solid-phase oxidizing the surface of the semiconductor film by plasma treatment shown here, an insulating film with excellent uniformity and low interface state density can be formed without unusual oxidizing reaction in the crystal grain boundary.

Note that only an insulating film formed by high-density plasma treatment may be used for the gate insulating film 1906, or an insulating film such as silicon oxide, silicon oxynitride, or silicon nitride may be deposited to be stacked thereover by CVD utilizing plasma or thermal reaction. In any case, in a transistor which is formed to include an insulating film formed by high-density plasma treatment in part or all of a gate insulating film, variations in characteristic can be reduced.

In addition, in the semiconductor films 1905a to 1905f which are obtained by scanning in one direction to be crystallized while the semiconductor films are irradiated with a continuous wave laser or laser beam which is emitted with a repetition rate of 10 MHz or more, characteristics such that crystals grow in a scan direction of the beam exist. When a transistor is arranged by adjusting the scan direction to a channel length direction (a direction in which a carrier flows when a channel formation region is formed) and the above-described gate insulating layer is used, a thin film transistor (a TFT) with little variations in characteristics and high field effect mobility can be obtained.

Next, a first conductive film and a second conductive film are stacked over the gate insulating film 1906. Here, the first conductive film is formed with a thickness of 20 to 100 nm by CVD, sputtering, or the like. The second conductive film is formed with a thickness of 100 to 400 nm. The first conductive film and the second conductive film are formed using an element selected from tantalum (Ta), tungsten (W), titanium (Ti), molybdenum (Mo), aluminum (Al), copper (Cu), chrome (Cr), niobium (Nb), or the like, or an alloy material or a compound material which includes any of these elements as a main component. Alternatively, the first conductive film and the second conductive film are formed using a semiconductor material typified by polycrystalline silicon doped with an impurity element such as phosphorus. As an example of a combination of the first conductive film and the second conductive film, a tantalum nitride film and a tungsten film, a tungsten nitride film and a tungsten film, a molybdenum nitride film and a molybdenum film, or the like can be given. Since tungsten and tantalum nitride have high thermal resistance, heat treatment aimed at thermal activation can be performed after the first conductive film and the second conductive film are formed. In addition, in the case of a three-layer structure, a stacked-layer structure of a molybdenum film, an aluminum film, and a molybdenum film may be used.

Next, a resist mask is formed by photolithography and a gate electrode 1907 is formed above each of the semiconductor films 1905a to 1905f by etching for forming the gate electrode and a gate line. Here, an example is shown in which a stacked-layer structure of a first conductive film 1907a and a second conductive film 1907b is provided as the gate electrode 1907.

Next, as shown in FIG. 6C, the semiconductor films 1905a to 1905f are doped with an impurity element which imparts n-type conductivity with low concentration by using the gate electrode as a mask by ion doping or ion implantation, and then, the resist mask is selectively formed by photolithography and the semiconductor films 1905a to 1905f are doped with an impurity element which imparts p-type conductivity with high concentration. As an impurity element which imparts n-type conductivity, phosphorus (P), arsenic (As), or the like can be used. As an impurity element which imparts p-type conductivity, boron (B), aluminum (Al), gallium (Ga), or the like can be used. Here, phosphorus (P) is used as the impurity element which imparts n-type conductivity, and phosphorus (P) is selectively introduced into the semiconductor films 1905a to 1905f so as to be included therein with a concentration of $1 \times 10^{15}$ to $1 \times 10^{19}/cm^3$ to form an impurity region 1908 having n-type conductivity. Further, boron (B) is used as the impurity element which imparts p-type conductivity, and boron (B) is selectively introduced into the semiconductor films 1905c and 1905e so as to be included therein with a concentration of $1 \times 10^{19}$ to $1 \times 10^{20}/cm^3$ to form an impurity region 1909 which imparts p-type conductivity.

Sequentially, a gate insulating film is formed so as to cover the semiconductor film 1906 and the gate electrode 1907. The insulating film is formed with a single-layer structure or a stacked-layer structure of a film including an inorganic material such as silicon, silicon oxide, or silicon nitride, or a film including an organic material such as an organic resin by plasma CVD, sputtering, or the like. Next, the insulating film is selectively etched by anisotropic etching which is based on a perpendicular direction to form an insulating film 1910 (also referred to as a sidewall) which is in contact with a side of the gate electrode 1907. The insulating film 1910 is used as a doping mask when a LDD (lightly doped drain) region is formed.

Sequentially, the semiconductor films 1905a, 1905b, 1905d, and 1905f are doped with an impurity element which imparts n-type conductivity with high concentration by using the resist mask, which is formed by photolithography as well as the gate electrode 1907 and the insulating film 1910 as masks, and an impurity region 1911 having n-type conductivity is formed. Here, phosphorus (P) is used as the impurity element which imparts n-type conductivity, and phosphorus (P) is selectively introduced into the semiconductor films 1905a, 1905b, 1905d, and 1905f so as to be included therein with a concentration of $1 \times 10^{19}$ to $1 \times 10^{20}$ cm$^3$ to form the impurity region 1911, the concentration of n-type impurity element of which is higher than that of the impurity region 1908.

By the above-described steps, as shown in FIG. 6D, n-channel thin film transistors 1900a, 1900b, 1900d, and 1900f and p-channel thin film transistors 1900c and 1900e are formed.

Note that in the n-channel thin film transistor 1900a, a channel formation region is formed in a region of the semiconductor film 1905a which overlaps with the gate electrode 1907; the impurity region 1911 forming a source region or a drain region is formed in a region of the semiconductor film 1905a which does not overlap with the gate electrode 1907 and the insulating film 1910; and a low concentration impurity region (an LDD region) is formed in a region of the semiconductor film 1905a which overlaps with the insulating film 1907 and between the channel formation region and the impurity region 1911. Similarly, in each of the n-channel thin film transistors 1900b, 1900d, and 1900f, a channel formation region, a low concentration impurity region, and the impurity region 1911 are formed.

In the p-channel thin film transistor 1900c, a channel formation region is formed in a region of the semiconductor film 1905c which overlaps with the gate electrode 1907 and the impurity region 1909 forming a source region or a drain region is formed in a region of the semiconductor film 1905a which does not overlap with the gate electrode 1907. Similarly, in the p-channel thin film transistor 1900e, a channel formation region and an impurity region 1909 are formed. Note that although an LDD region is not provided in each of the p-channel thin film transistors 1900c and 1900e here, an LDD region may be provided in each of the p-channel thin film transistors or a structure in which an LDD region is not provided in each of the n-channel thin film transistors may also be used.

Figure 7A:
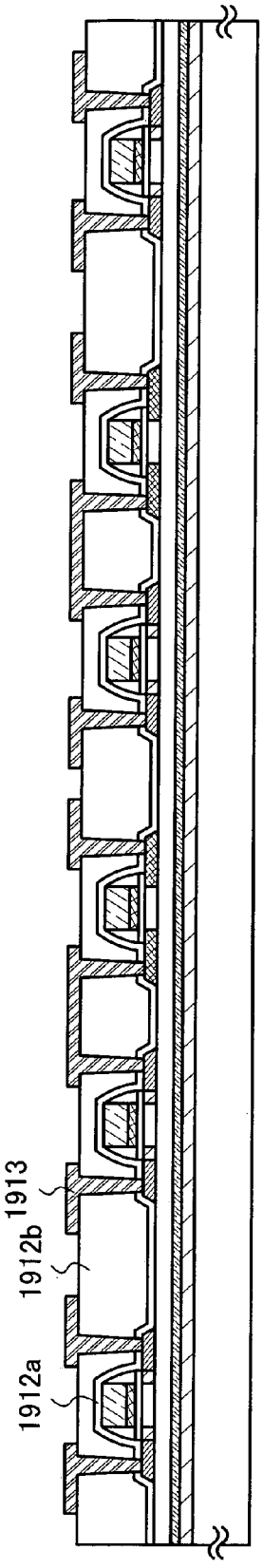
FIGS. 7A and 7B illustrate manufacturing steps of an assist device of the present invention.

Next, as shown in FIG. 7A, an insulating film is formed with a single-layer structure or a stacked-layer structure so as to cover the semiconductor films 1905a to 1905f, the gate electrode 1907, and the like, and conductive films 1913 which are electrically connected to the impurity regions 1909 and 1911 forming the source regions or the drain regions of the thin film transistors 1900a to 1900f are formed over the insulating film. The insulating film is formed with a single-layer structure or a stacked-layer structure using an inorganic material such as silicon oxide or silicon nitride, an organic material such as polyimide, polyamide, benzocyclobutene, acryl, or epoxy, a siloxane material, or the like by CVD, sputtering, SOG, a droplet discharge method, a screen printing method, or the like. The insulating film is formed with a two-layer structure, and a silicon nitride oxide film is formed as a first-layer insulating film 1912a and a silicon oxynitride film is formed as a second-layer insulating film 1912b. In addition, the conductive films 1913 form source electrodes or drain electrodes of the thin film transistors 1900a to 1900f.

Note that heat treatment aimed at recovery of crystallinity of the semiconductor films, activation of the impurity element which has been added to the semiconductor films, or hydrogenation of the semiconductor films may be performed before the insulating films 1912a and 1912b are formed or after one or a plurality of thin films of the insulating films 1912a and 1912b are formed. Thermal anneal, laser anneal, RTA, or the like may be applied to heat treatment.

The conductive film 1913 is formed with a single-layer structure or a stacked-layer structure of an element selected from aluminum (Al), tungsten (W), titanium (Ti), tantalum (Ta), molybdenum (Mo), nickel (Ni), platinum (Pt), copper (Cu), gold (Au), silver (Ag), manganese (Mn), neodymium (Nd), carbon (C), or silicon (Si), or an alloy material or a compound material which includes any of these elements as a main component. An alloy material which includes aluminum as a main component corresponds to a material which includes aluminum as a main component and includes nickel, or an alloy material which includes aluminum as a main component and includes nickel and one of or both carbon and silicon, for example. For the conductive film 1913, a stacked-layer structure of a barrier film, an aluminum silicon film, and a barrier film or a stacked-layer structure of a barrier film, an aluminum silicon film, a titanium nitride film, and a barrier film may be used, for example. Note that a barrier film corresponds to a thin film formed using titanium, titanium nitride, molybdenum, or molybdenum nitride. Since aluminum and aluminum silicon have low resistance values and are inexpensive, aluminum and aluminum silicon are suitable for a material for forming the conductive film 1913. In addition, when the barrier films are provided in an upper layer and a lower layer, generation of a hillock of aluminum or aluminum silicon can be prevented. Further, when a barrier film is formed with titanium which is an element having a high reducing property, even when a thin natural oxide film is formed over the crystalline semiconductor films, the natural oxide film can be chemically reduced and an excellent contact with the crystalline semiconductor films can be obtained.

Next, an insulating film 1914 is formed so as to cover the conductive films 1913, and conductive films 1915a and 1915b which are each electrically connected to the conductive films 1913 forming the source electrodes or the drain electrodes of the thin film transistors 1900a and 1900f are formed over the insulating film 1914. In addition, conductive films 1916a and 1916b which are each electrically connected to the conductive films 1913 forming the source electrodes or the drain electrodes of the thin film transistors 1900b and 1900e are formed. Note that the conductive films 1915a and 1915b and the conductive films 1916a and 1916b may be formed by using the same material and at the same time. The conductive films 1915a and 1915b and the conductive films 1916a and 1916b can be formed with any of the materials described for the conductive film 1913.

Figure 7B:
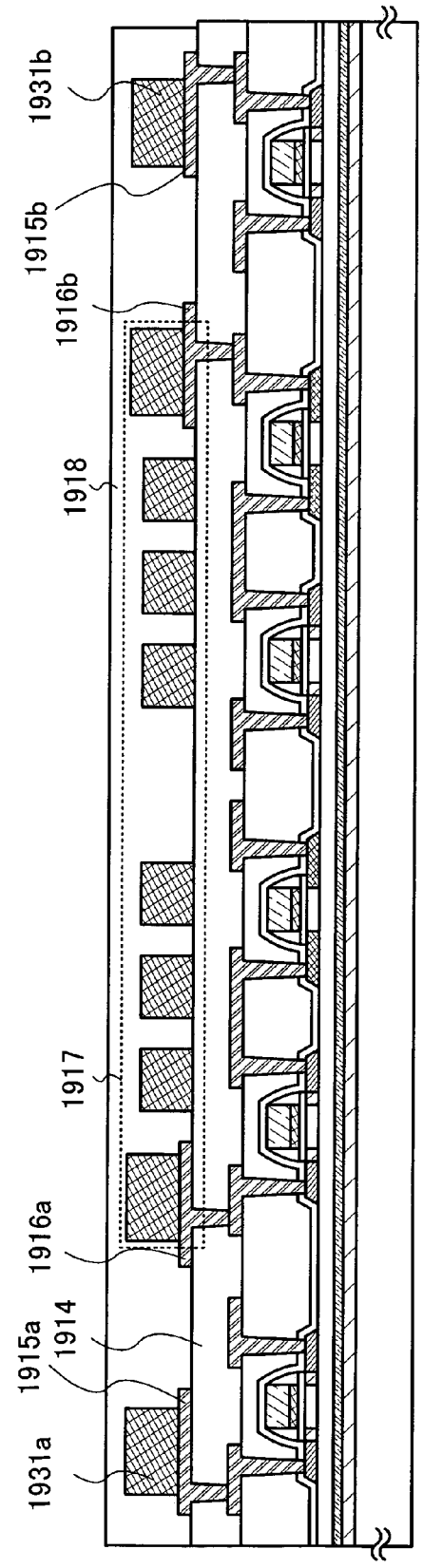

Subsequently, as shown in FIG. 7B, a conductive film 1917 functioning as an antenna is formed so as to be electrically connected to the conductive films 1916a and 1916b. At the same time as forming the conductive film 1917 functioning as an antenna, conductive films 1931a and 1931b which are electrically connected to the conductive films 1915a and 1915b respectively are formed. Here, the conductive film 1917 functioning as an antenna corresponds to the antenna described in the aforementioned embodiment mode. In addition, the thin film transistors 1900b to 1900e function as the transmitting/receiving circuits described in the aforementioned embodiment mode. Further, the conductive films 1931a and 1931b can function as wirings which are electrically connected to the battery in a latter step. Next, an insulating film 1918 which covers the conductive films 1917, 1931a, and 1931b is formed.

Further, although not shown, when the conductive film 1917 functioning as an antenna is formed, a conductive film is separately formed so as to be electrically connected to the amplifier circuit 106, and the conductive film is used as a wiring which is connected to the myoelectric potential electrode 104 and the reference electrode 105 shown in FIG. 2.

The conductive films 1917, 1931a, and 1931b are formed using a conductive material by using CVD, sputtering, a printing method such as a screen printing method or a gravure printing method, a droplet discharge method, a dispenser method, a metal plating method, or the like. The conductive material is formed with a single-layer structure or a stacked-layer structure of an element selected from aluminum (Al), titanium (Ti), silver (Ag), copper (Cu), gold (Au), platinum (Pt), nickel (Ni), palladium (Pd), tantalum (Ta), or molybdenum (Mo), or an alloy material or a compound material which includes any of these elements as a main component.

For example, in the case of forming the conductive film 1917 functioning as the antenna by using the screen printing method, the conductive film 1917 can be provided by selectively printing a conductive paste where a conductive particle having a particle size of several nm to several ten μm is dissolved or dispersed in an organic resin. As the conductive particle, metal particles of one or more of silver (Ag), gold (Au), copper (Cu), nickel (Ni), platinum (Pt), palladium (Pd), tantalum (Ta), molybdenum (Mo), titanium (Ti), and the like, a fine particle of silver halide, or a dispersing nano particle can be used. In addition, as the organic resin included in the conductive paste, one or more selected from organic resins functioning as a binder, a solvent, a dispersive agent, and a coating member of the metal particles can be used. Typically, an organic resin such as an epoxy resin or a silicone resin can be given as an example of the organic resin included in the conductive paste. Further, in forming the conductive film, baking is preferably performed after the conductive paste is pushed out. For example, in the case of using a fine particle which includes silver as a main component (for example, a particle size is equal to or greater than 1 nm and equal to or less than 100 nm) as a material for the conductive paste, the conductive film can be obtained by baking it with temperatures in the range of 150 to 300° C. to cure. Further, a fine particle which includes solder or lead-free solder as a main component may also be used. In this case, it is preferable that a fine particle having a particle size of 20 μm or less be used. Solder or lead-free solder has an advantage such as low cost.

The insulating films 1914 and 1918 can be provided with a single-layer structure or a stacked-layer structure formed using an insulating film including oxygen or nitrogen such as silicon oxide, silicon nitride, silicon oxynitride, or silicon nitride oxide, a film including carbon such as DLC (diamond like carbon), an organic material such as epoxy, polyimide, polyamide, polyvinyl phenol, benzocyclobutene, or acryl, or a siloxane material such as a siloxane resin.

Next, as shown in FIG. 8A, opening portions 1932a and 1932b are formed in the insulating film 1918 so that surfaces of the conductive films 1931a and 1931b are exposed.

Next, in this embodiment mode, opening portions are formed in a layer which includes the thin film transistors 1900a to 1900f, the conductive film 1917, the insulating film 1918, and the like (hereinafter described as an element formation layer 1919) by laser light irradiation.

Next, after an adhesive material 1920 is attached to one surface of the element formation layer 1919 (a surface in which the insulating film 1918 is exposed), the element formation layer 1919 is separated from the substrate 1901. Here, the element formation layer 1919 can be separated from the substrate 1901 by using physical force after an opening portion is formed in a region excluding the thin film transistors 1900a to 1900f by laser light irradiation (e.g., UV light). Alternatively, before the element formation layer 1919 is separated from the substrate 1901, the separation layer 1903 may be selectively removed by introducing an etching agent into the formed opening portion. Gas or liquid including halogen fluoride or an interhalogen compound is used as the etching agent. For example, chlorine trifluoride (ClF$_3$) is used as the gas including halogen fluoride. Then, the element formation layer 1919 is in the condition that it is separated from the substrate 1901. Note that the separation layer 1903 may be partially kept without being removed entirely. Therefore, consumption of the etching agent can be suppressed and a processing time which is necessary for removing the separation layer 1903 can be shortened. In addition, the element formation layer 1919 can be held over the substrate 1901 even after the separation layer 1903 is separated from the substrate 1901. Further, when the substrate 1901 from which the element formation layer 1919 is separated is recycled, cost can be reduced.

Figure 9A:
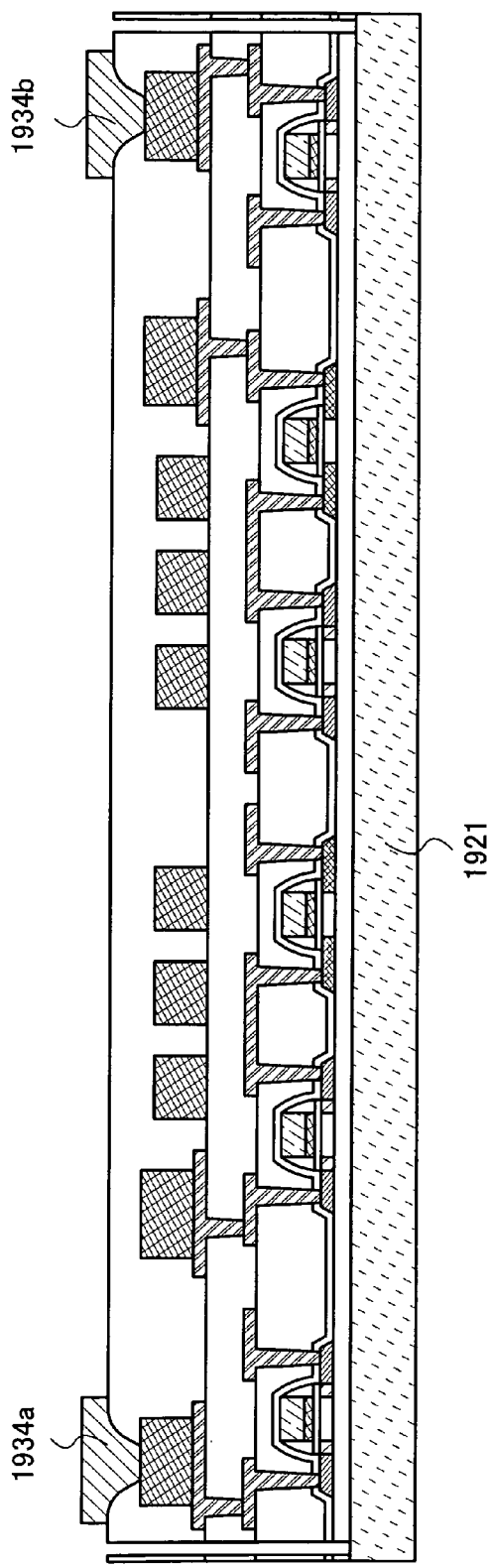
FIGS. 9A and 9B illustrate manufacturing steps of an assist device of the present invention.

Next, as shown in FIG. 9A, after a first housing 1921 is attached to the other surface of the element formation layer 1919 (a surface which is exposed by separation), the element formation layer 1919 is separated from the adhesive material 1920. Accordingly, here, an adhesive material having weak adhesiveness is used as the adhesive material 1920. Subsequently, conductive films 1934a and 1934b which are electrically connected to the conductive films 1931a and 1931b through the opening portions 1932a and 1932b respectively are selectively formed.

A material and a formation method which are similar to those of the conductive film 1917 can be used for the conductive films 1934a and 1934b as appropriate.

Note that here, although an example is shown in which the conductive films 1934a and 1934b are formed after the element formation layer 1919 is separated from the substrate 1901, the element formation layer 1919 may be separated from the substrate 1901 after the conductive films 1934a and 1934b are formed.

The first housing 1921 is formed using a biologically inactive material. Typically, a housing formed using a conductive material such as titanium, platinum, or gold, or a housing formed using an insulating material such as an organic resin or ceramic may be used. Alternatively, a film formed using any of the above-described materials may be used as the first housing 1921. When a film is used as the first housing 1921, the artificial limb driving portion 223, which is thin, lightweight, and can be easily fit in the body with little irregularity, can be manufactured.

Further alternatively, a material to which countermeasures against static electricity is applied in order to prevent static electricity or the like (hereinafter described as an antistatic material) can be used as the first housing 1921. As the antistatic material, metal, indium tin oxide (ITO), and a surface active agent such as an ampholytic surface active agent, a cationic surface active agent, or a nonionic surface active agent can be used. Alternatively, as the antistatic material, a resin material including a cross-linking polymer which has a carboxyl group and quaternary ammonium base as a side chain or the like can also be used. When such a material is attached to the housing, kneading such a material into the housing, or coating the housing with such a material, electrification can be prevented.

Figure 9B:
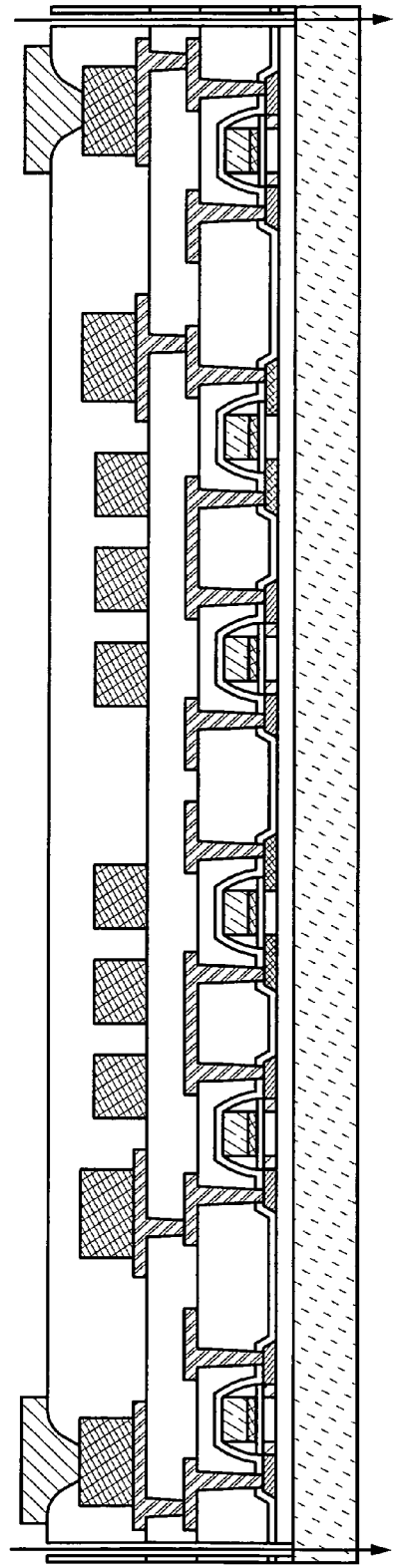

Next, as shown in FIG. 9B, in the case where a plurality of elements are formed over the substrate, the element formation layer 1919 is cut into each element. Cutting can be performed by using a laser irradiation apparatus, a dicing apparatus, a scribe apparatus, or the like. Here, the plurality of elements formed over one substrate are cut respectively by laser light irradiation.

Next, as shown in FIG. 10A, the cut elements are electrically connected to connection terminals of the battery. Although not shown, the amplifier circuit 106 and the myoelectric potential electrode 104 are electrically connected. In addition, the amplifier circuit 106 and the reference electrode 105 are electrically connected. Here, an example is shown in which the conductive films 1934a and 1934b provided in the element formation layer 1919 are connected to conductive films 1936a and 1936b which are provided on a substrate 1935 and serve as connection terminals of the battery, respectively. Here, for connection between the conductive film 1934a and the conductive film 1936a or connection between the conductive film 1934b and the conductive film 1936b, the case is shown in which the conductive film 1934a and the conductive film 1936a or the conductive film 1934b and the conductive film 1936b are electrically connected by pressure bonding with a material having adhesiveness such as an ACF (anisotropic conductive film) or an ACP (anisotropic conductive paste). Here, an example is shown in which the conductive film 1934a and the conductive film 1936a or the conductive film 1934b and the conductive film 1936b are connected by using conductive particles 1938 included in a resin 1937 having adhesiveness. In addition, the conductive film 1934a and the conductive film 1936a or the conductive film 1934b and the conductive film 1936b can be connected by using a conductive adhesive agent such as a silver paste, a copper paste, or a carbon paste, a solder junction, or the like.

Next, as shown in FIG. 10B, after a second housing 1922 is attached to the other surface of the element formation layer 1919 (the surface which is exposed by separation) and the battery, the first housing 1921 and the second housing 1922 are attached to each other by performing one of or both heat treatment and pressure treatment. Any of the materials for the first housing 1921 can be used for the second housing 1922 as appropriate. Note that when the first housing 1921 and the second housing 1922 are attached to each other, the myoelectric potential electrode 104 and the reference electrode 105 are provided so as to protrude outside of the housings. In addition, the first housing 1921 and the second housing 1922 may be attached to each other so as to obtain vacuum therebetween.

Further, when surfaces of the first housing 1921 and the second housing 1922 are protected with a protective layer formed using silicon, a fluoride resin, parylene, DLC, or the like, safety of the human body is further increased.

Note that connection between the battery 119 and the charging circuit 118, connection between the myoelectric potential electrode 104 and the amplifier circuit 106, and connection between the reference electrode 105 and the amplifier circuit 106 may be performed before the element formation layer 1919 is separated from the substrate 1901 (a stage of FIG. 8A or FIG. 8B), or may be performed after the element formation layer 1919 is sealed with the first housing 1921 and the second housing 1922 (a stage of FIG. 10B).

In the case where the battery is larger than the elements, as shown in FIGS. 9A and 9B, and FIGS. 10A and 10B, a plurality of elements are formed over one substrate and the elements are connected to the battery after separation, so that the number of elements formed over one substrate can be increased. Therefore, the assist device 101 can be manufactured at lower cost.

By the above-described steps, the myoelectric potential detecting portion 222 of the myoelectric artificial limb 211 can be manufactured. Note that although a step in which separation is performed after an element such as a thin film transistor is formed over a substrate is shown in this embodiment mode, the myoelectric potential detecting portion 222 of the myoelectric artificial limb 211 may be directly commercialized without performing separation. Further, after an element such as a thin film transistor is formed over a glass substrate, the glass substrate is polished from a surface which is opposite to a surface over which the element is formed; or after a MOS transistor is formed using a semiconductor substrate formed using Si or the like, the semiconductor substrate is polished. Thus, the myoelectric potential detecting portion 222 of the myoelectric artificial limb 211 can be thinned and made smaller.

Note that the method for manufacturing the myoelectric potential detecting portion 222 of the myoelectric artificial limb 221 described in this embodiment mode can be applied to the method for manufacturing the detecting portion 102 of the assist device 101 described in other embodiment modes in this specification. Note that in the case of the detecting portion 102, it is acceptable as long as the first sensor 100 is provided instead of the myoelectric potential detecting portion 222.

This application is based on Japanese Patent Application serial No. 2007-029916 filed with Japan Patent Office on Feb. 9, 2007, the entire contents of which are hereby incorporated by reference.

What is claimed is:

1. An assist device comprising a detecting portion and a first driving portion which is an assist device driving portion,
   wherein the detecting portion comprises:
      a first data processing circuit;
      a sensor connected to the first data processing circuit;
      a first transmitting and receiving circuit connected to the first data processing circuit;
      a first charging circuit connected to the first transmitting and receiving circuit;
      a first battery connected to the first charging circuit with an anisotropic conductive paste; and
      a first antenna connected to the first transmitting and receiving circuit,
   wherein the assist device driving portion comprises:
      a second data processing circuit;
      a second driving portion connected to the second data processing circuit;
      a second transmitting and receiving circuit connected to the second data processing circuit;
      a second battery connected to the second data processing circuit;
      a second charging circuit connected to the second battery; and
      a second antenna connected to the second transmitting and receiving circuit,
   wherein each of the first data processing circuit, the first transmitting and receiving circuit, and the first charging circuit comprises a thin film transistor,
   wherein the first antenna is provided between the first battery and the thin film transistors included in each of the first data processing circuit, the first transmitting and receiving circuit, and the first charging circuit,
   wherein the first data processing circuit, the first transmitting and receiving circuit, the first charging circuit, and the first battery are surrounded with a first housing and a second housing,
   wherein each of the first housing and the second housing is protected with a protective layer,
   wherein the first antenna and the second antenna are configured to transmit an electromagnetic wave therebetween,
   wherein the second driving portion comprises a movable skeleton, a fixed skeleton, and a driving unit,
   wherein the movable skeleton and the fixed skeleton are combined with a joint mechanism, and
   wherein the driving unit is provided in the fixed skeleton.

2. An assist device according to claim 1,
   wherein the assist device driving portion is an artificial limb driving portion.

3. An assist device according to claim 1,
wherein the first antenna is provided over the first transmitting and receiving circuit.

4. An assist device according to claim 1,
wherein the assist device is water-resistant.

5. An assist device according to claim 1,
wherein the first antenna, the first charging circuit, and the first transmitting and receiving circuit are formed over a substrate.

6. An assist device according to claim 1,
wherein the first antenna is a dipole antenna.

7. An assist device according to claim 1,
wherein the sensor comprises a myoelectric potential electrode and a reference electrode, and
wherein the myoelectric potential electrode and the reference electrode are provided so as to protrude outside of the first housing and the second housing.

8. An assist device according to claim 1,
wherein the first antenna is a patch antenna.

9. An assist device according to claim 1, wherein the second battery is charged from one of an external power supply and an AC current, and
wherein the AC current is generated in the second transmitting and receiving circuit by receiving electromagnetic waves at the second antenna.

10. An assist device comprising a detecting portion and a first driving portion which is an assist device driving portion,
wherein the detecting portion comprises:
   a first central arithmetic processing circuit;
   an A/D converter circuit connected to the first central arithmetic processing circuit;
   an amplifier circuit connected to the ND converter circuit;
   a first sensor connected to the amplifier circuit;
   a first transmitting and receiving circuit connected to the first central arithmetic processing circuit;
   a first charging circuit connected to the first transmitting and receiving circuit;
   a first battery connected to the first charging circuit with an anisotropic conductive paste; and
   a first antenna connected to the first transmitting and receiving circuit,
wherein the assist device driving portion comprises:
   a second central arithmetic processing circuit;
   a drive control circuit connected to the second central arithmetic processing circuit;
   a second battery connected to the second central arithmetic processing circuit;
   a second driving portion connected to the second battery and the drive control circuit;
   a second sensor connected to the second central arithmetic processing circuit;
   a second charging circuit connected to the second battery;
   a second transmitting and receiving circuit connected to the second central arithmetic processing circuit and the second battery and the second charging circuit; and
   a second antenna connected to the second transmitting and receiving circuit,
wherein each of the first central arithmetic processing circuit, the A/D converter circuit, the amplifier circuit, the first transmitting and receiving circuit, and the first charging circuit comprises a thin film transistor,
wherein the first antenna is provided between the first battery and the thin film transistors included in each of the first central arithmetic processing circuit, the A/D converter circuit, the amplifier circuit, the first transmitting and receiving circuit, and the first charging circuit,
wherein the first central arithmetic processing circuit, the ND converter circuit, the amplifier circuit, the first transmitting and receiving circuit, the first charging circuit, and the first battery are surrounded with a first housing and a second housing,
wherein each of the first housing and the second housing is protected with a protective layer,
wherein the first antenna and the second antenna are configured to transmit an electromagnetic wave therebetween,
wherein the second driving portion comprises a movable skeleton, a fixed skeleton, and a driving unit,
wherein the movable skeleton and the fixed skeleton are combined with a joint mechanism, and
wherein the driving unit is provided in the fixed skeleton.

11. An assist device according to claim 10,
wherein the first battery supplies power to an inside of the detecting portion, and
wherein the second battery supplies power to an inside of the assist device driving portion.

12. An assist device according to claim 10,
wherein the assist device driving portion is an artificial limb driving portion.

13. An assist device according to claim 10, wherein the second battery is charged from an external power supply through the second charging circuit.

14. An assist device according to claim 10, wherein the first battery is charged from electromagnetic waves received by the first transmitting and receiving circuit through the first charging circuit.

15. An assist device according to claim 10,
wherein the first antenna is provided over the first transmitting and receiving circuit.

16. An assist device according to claim 10,
wherein the assist device is water-resistant.

17. An assist device according to claim 10,
wherein the first antenna, the first charging circuit, and the first transmitting and receiving circuit are formed over a substrate.

18. An assist device according to claim 10,
wherein the first antenna is a dipole antenna.

19. An assist device according to claim 10,
wherein the first sensor comprises a myoelectric potential electrode and a reference electrode, and
wherein the myoelectric potential electrode and the reference electrode are provided so as to protrude outside of the first housing and the second housing.

20. An assist device according to claim 10,
wherein the first antenna is a patch antenna.

21. An assist device according to claim 10, wherein the second battery is charged from one of an external power supply and an AC current, and
wherein the AC current is generated in the second transmitting and receiving circuit by receiving electromagnetic waves at the second antenna.

* * * * *

UNITED STATES PATENT AND TRADEMARK OFFICE
CERTIFICATE OF CORRECTION

PATENT NO. : 8,585,775 B2  
APPLICATION NO. : 12/068451  
DATED : November 19, 2013  
INVENTOR(S) : Takashi Izumi et al.

Page 1 of 1

It is certified that error appears in the above-identified patent and that said Letters Patent is hereby corrected as shown below:

In the Specification

Column 26, line 34, "ofYAG;" should be --of YAG,--;

In the Claims

Claim 10, column 35, line 33, "ND" should be --A/D--; and

Claim 10, column 36, line 9, "ND" should be --A/D--.

Signed and Sealed this
Eighteenth Day of February, 2014

Michelle K. Lee
*Deputy Director of the United States Patent and Trademark Office*